United States Patent
Von Stein et al.

(10) Patent No.: US 8,895,522 B2
(45) Date of Patent: *Nov. 25, 2014

(54) COMPOSITION AND METHOD FOR THE PREVENTION, TREATMENT AND/OR ALLEVIATION OF AN INFLAMMATORY DISEASE

(75) Inventors: Oliver Von Stein, Upplands Väsby (SE); Karin Hellström, Trosa (SE)

(73) Assignee: Index Pharmaceuticals AB, Stockholm (SE)

( * ) Notice: Subject to any disclaimer, the term of this patent is extended or adjusted under 35 U.S.C. 154(b) by 784 days.

This patent is subject to a terminal disclaimer.

(21) Appl. No.: 12/090,477

(22) PCT Filed: Oct. 27, 2006

(86) PCT No.: PCT/SE2006/050433
§ 371 (c)(1),
(2), (4) Date: Sep. 19, 2008

(87) PCT Pub. No.: WO2007/050034
PCT Pub. Date: May 3, 2007

(65) Prior Publication Data
US 2010/0004319 A1 Jan. 7, 2010

Related U.S. Application Data

(60) Provisional application No. 60/731,373, filed on Oct. 28, 2005.

(51) Int. Cl.
*A61K 48/00* (2006.01)
*A61K 31/56* (2006.01)
*A61K 31/7088* (2006.01)

(52) U.S. Cl.
CPC ............. *A61K 31/56* (2013.01); *A61K 31/7088* (2013.01)
USPC ............................................ 514/44; 536/24.5

(58) Field of Classification Search
CPC ............................ C12N 15/111; C12N 15/113
See application file for complete search history.

(56) References Cited

U.S. PATENT DOCUMENTS

| | | | |
|---|---|---|---|
| 5,366,878 A | 11/1994 | Pederson et al. | |
| 5,591,840 A | 1/1997 | Narayanan et al. | |
| 5,635,377 A | 6/1997 | Pederson et al. | |
| 5,652,355 A | 7/1997 | Metelev et al. | |
| 6,133,246 A * | 10/2000 | McKay et al. ............... | 514/44 A |
| 6,143,881 A | 11/2000 | Metelev et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,294,382 B1 | 9/2001 | Bennett et al. | |
| 6,339,068 B1 | 1/2002 | Krieg et al. | |
| 6,346,614 B1 | 2/2002 | Metelev et al. | |
| 6,406,705 B1 | 6/2002 | Davis et al. | |
| 6,426,334 B1 | 7/2002 | Agrawal et al. | |
| 6,426,336 B1 | 7/2002 | Carson et al. | |
| 6,429,199 B1 | 8/2002 | Krieg et al. | |
| 6,589,940 B1 | 7/2003 | Raz et al. | |
| 6,653,292 B1 | 11/2003 | Krieg et al. | |
| 6,943,240 B2 | 9/2005 | Bauer et al. | |
| 6,949,520 B1 | 9/2005 | Hartmann et al. | |
| 7,223,398 B1 | 5/2007 | Tuck et al. | |
| 2002/0198165 A1 | 12/2002 | Bratzler et al. | |
| 2003/0026801 A1 | 2/2003 | Weiner et al. | |
| 2003/0050268 A1 | 3/2003 | Krieg et al. | |
| 2003/0055014 A1 | 3/2003 | Bratzler | |
| 2003/0078223 A1 | 4/2003 | Raz et al. | |
| 2003/0087848 A1* | 5/2003 | Bratzler et al. ................. | 514/44 |
| 2003/0166001 A1 | 9/2003 | Lipford et al. | |
| 2003/0191079 A1 | 10/2003 | Krieg et al. | |
| 2003/0212026 A1 | 11/2003 | Krieg et al. | |
| 2003/0232074 A1 | 12/2003 | Lipford et al. ................ | 424/450 |
| 2004/0030118 A1 | 2/2004 | Wagner et al. | |
| 2004/0043023 A1 | 3/2004 | Vedeckis et al. | |
| 2004/0131628 A1 | 7/2004 | Bratzler et al. | |
| 2004/0234969 A1 | 11/2004 | Yuji et al. | |

(Continued)

FOREIGN PATENT DOCUMENTS

EP 0468520 A2 1/1992
EP 589330 A2 3/1994

(Continued)

OTHER PUBLICATIONS

Yacyshyn, et al, Double blind, placebo controlled trial of the remission inducing and steroid sparing properties of an ICAM-1 antisense oligodeoxynucleotide, alicaforsen (ISIS 2302), in active steroid dependent Crohn's disease, GUT, (2002), 51:30-36.
Ikeda et al., Resolution of Airway Inflammation following Ovalbumin Inhalation, American Journal of Respiratory Cell and Molecular Biology, vol. 28, 2003, 655-663.
Sun et al., Change of Nuclear Protein Level of GR, AP-1 and NF-kB During the Glucocorticoid Treatment in Idiopathic Nephrotic Syndrome, Fudan Univ J Med Sci, Sep. 2003, 418-421.
Hartmann et al., Mechanism and Function of a Newly Identified CpG DNA Motif in Human Primary B Cells, Journal of Immunology, 2000, 944-952.
Aviles et al., Decreased Expression of T-cell NF-kB p65 Subunit in Steroid-Resistant Nephrotic Syndrome, Kidney International, vol. 66, 2004, 60-67.

(Continued)

*Primary Examiner* — Kimberly Chong
(74) *Attorney, Agent, or Firm* — Porter Wright Morris & Arthur LLP

(57) ABSTRACT

A method for enhancing the clinical responsiveness to an anti-inflammatory therapy in a patient afflicted with an inflammatory condition, comprising administering an oligonucleotide having the sequence 5'-Xm-CG-Yn-3' in an effective amount to said patient, and wherein X is A, T, C or G; Y is A, T, C or G; m=1-40; n=1-40 and wherein at least one CG dinucleotide is unmethylated. The invention also encompasses the use of such an oligonucleotide for the manufacture of a medicament for enhancing steroid efficacy in the treatment of a patient afflicted with an inflammatory condition.

58 Claims, 15 Drawing Sheets

(56) References Cited

U.S. PATENT DOCUMENTS

| | | |
|---|---|---|
| 2004/0235770 A1 | 11/2004 | Davis et al. |
| 2004/0266719 A1 | 12/2004 | McCluskie et al. |
| 2005/0158325 A1* | 7/2005 | Hammerbeck et al. .... 424/155.1 |
| 2005/0175630 A1 | 8/2005 | Raz et al. |
| 2005/0238660 A1 | 10/2005 | Babiuk et al. |
| 2006/0189550 A1* | 8/2006 | Jiang et al. ................. 514/26 |
| 2006/0211639 A1 | 9/2006 | Bratzler et al. |
| 2006/0229271 A1 | 10/2006 | Krieg et al. |
| 2006/0251677 A1 | 11/2006 | Bachmann et al. |
| 2006/0257851 A1 | 11/2006 | Bentwich |
| 2006/0287261 A1 | 12/2006 | Agrawal et al. |
| 2009/0155307 A1 | 6/2009 | Davis et al. |
| 2009/0191188 A1* | 7/2009 | Krieg et al. ................ 424/130.1 |

FOREIGN PATENT DOCUMENTS

| | | | |
|---|---|---|---|
| EP | 1078053 B1 | 9/2005 | |
| EP | 0772619 B1 | 6/2006 | |
| EP | 0948510 B1 | 7/2006 | |
| EP | 1220684 B1 | 7/2006 | |
| EP | 1077722 B1 | 8/2006 | |
| EP | 1688147 A1 | 8/2006 | |
| EP | 1700603 A2 | 9/2006 | |
| EP | 1714969 A2 | 10/2006 | |
| EP | 1746159 A2 | 1/2007 | |
| EP | 1067956 B1 | 3/2007 | |
| EP | 1296714 B1 | 8/2009 | |
| EP | 1005368 B1 | 9/2009 | |
| JP | 2008-535859 A | 9/2008 | |
| WO | 96/02555 A1 | 2/1996 | |
| WO | 97/28259 A1 | 8/1997 | |
| WO | WO 97/47325 | 12/1997 | ............ A61K 38/00 |
| WO | 98/16247 A1 | 4/1998 | |
| WO | 98/37919 A | 9/1998 | |
| WO | 99/56755 A | 11/1999 | |
| WO | 99/58118 A | 11/1999 | |
| WO | 99/62923 A | 12/1999 | |
| WO | 00/06588 A1 | 2/2000 | |
| WO | 01/22972 A2 | 4/2001 | |
| WO | 01/22990 A2 | 4/2001 | |
| WO | 01/68117 A2 | 9/2001 | |
| WO | 01/97843 A1 | 12/2001 | |
| WO | 02/22809 A2 | 3/2002 | |
| WO | 02/053141 A1 | 7/2002 | |
| WO | WO 02/085308 | 10/2002 | ............ A61K 31/122 |
| WO | 2004/058159 A2 | 7/2004 | |
| WO | 2004/058179 A2 | 7/2004 | |
| WO | 2004/064782 A2 | 8/2004 | |
| WO | 2004/087203 A2 | 10/2004 | |
| WO | 2004/103301 A2 | 12/2004 | |
| WO | 2005/080567 A1 | 9/2005 | |
| WO | 2005/080568 A1 | 9/2005 | |
| WO | 2005/081847 A2 | 9/2005 | |
| WO | 2006/002038 A2 | 1/2006 | |
| WO | 2006/015560 A1 | 2/2006 | |
| WO | 2006/028742 A2 | 3/2006 | |
| WO | WO 2007/004977 | 1/2007 | ............ A61K 38/00 |
| WO | WO 2007/004979 | 1/2007 | ............ A61K 38/00 |

OTHER PUBLICATIONS

Chikanza et al., Corticosteroid Resistance in Rheumatoid Arthritis: Molecular and Cellular Perspectives, Rheumatology, 2004, 43: 1337-1345.

Hauk et al., Increased Glucocorticoid Receptor β Expression Converts Mouse Hybridoma Cells to a Corticosteroid-Insensitive Phenotype, American Journal of Respiratory Cell and Molecular Biology, vol. 27, 2002, 361-367.

Leung et al., Update on Glucocorticoid Action and Resistance, J Allergy Clin Immunol, Jan. 2003, 3-22.

Agrawal et al., Medicinal Chemistry and Therapeutic Potential of CpG DNA, Trends in Molecular Medicine, vol. 8, No. 3, Mar. 2002, 114-121.

Bauer et al., Bacterial CpG-DNA Triggers Activation and Maturation of Human CD11c-, CD123+ Dendritic Cells, Journal of Immunology, 2001, 5000-5007.

Jahn-Schmid et al., Oligodeoxynucleotides Containing CpG Motifs Modulate the Allergic TH2 Response of BALB/c Mice to Bet v 1, the Major Birch Pollen Allergen, J Allergy Clin Immunol, 1999, 1015-1023.

Klinman, et al., CpG Motifs as Immune Adjuvants, Vaccine 17, 1999, 19-25.

Krug et al., Toll-like Recepter Expression Reveals CpG DNA as a Unique Microbial Stimulus for Plasmacytoid Dendritic Cells Which Synergizes with CD40 Ligand to Induce High Amounts of IL-12, Eur. J. Immunol. 2001. 31: 3026-3037.

Tighe et al., Conjugation of Protein to Immunostimulatory DNA Results in a Rapid, Long-lasting and Potent Induction of Cell-Mediated and Humoral Immunity, Eur. J. Immumol. 2000. 30: 1939-1947.

Tokunaga et al., Synthetic Oligonucleotides with Particular Base Sequences from the cDNA Encoding Proteins of *Mycobacterium bovis* BCG Induce Interferons and Activate Natural Killer Cells, Microbiol. Immunol., vol. 36 (1), 1992, 55-66.

Yamamoto et al., Unique Palindromic Sequences in Synthetic Oligonucleotides are Required to Induce INF and Augment INF-Mediated Natural Killer Activity, Journal of Immunology, 1992, vol. 148, 4072-4076.

Musch et al., Induction and Maintenance of Clinical Remission by Interferon—β in Patients with Steroid-Refractory Active Ulcerative Colitis and Open Long-Term Pilot Trial, Aliment Pharmacol Ther, 2002: 16: 1233-1239.

Simon et al., Clinical and Immunological Effects of Low-Dose IFN-α Treatment in Patients with Corticosteroid-Resistant Asthma, Allergy, 2003: 58: 1250-1255.

Hawrylowicz et al., Potential Role of Interleukin-10-Secreting Regulatory T Cells in Allergy and Asthma, Nature Reviews Immunology, vol. 5, 2005, 271-283.

Dean, et al., "Antisense oligonucleotide-based therapeutics for cancer", Oncogene, 2003, vol. 22, 9087-9096.

\* cited by examiner

COMPOSITION AND METHOD FOR THE PREVENTION, TREATMENT AND/OR ALLEVIATION OF AN INFLAMMATORY DISEASE

CROSS REFERENCE TO RELATED APPLICATIONS

This application is a 35 USC §371 National Stage application of International Application No. PCT/SE2006/050433 filed Oct. 27, 2006; which claims the benefit under 35 USC §119(e) to U.S. Application Ser. No. 60/731,373 filed Oct. 28, 2005, now abandoned. The disclosure of each of the prior applications is considered part of and is incorporated by reference in the disclosure of this application.

FIELD OF THE INVENTION

The present invention relates to the prevention, treatment and/or alleviation of inflammatory diseases, and in particular inflammatory conditions in the airways of a mammal, and more particular in human subjects that fail to show an adequate response to anti-inflammatory treatments.

BACKGROUND

Inflammation can be defined as an immunologic response to injury or irritation, characterized by local mobilization of white blood cells and antibodies, swelling, and fluid accumulation. This is a response that is identical whether the injurious agent is a pathogenic organism, foreign body, ischemia, physical trauma, ionizing radiation, electrical energy or extremes of temperature. Although a defense and repair mechanism of the body, the reactions produced during inflammation may be harmful and develop into e.g. chronic inflammation, hypersensitivity reactions, systemic or local inflammatory diseases. An inflammatory disease is in this context defined as a disease characterized by inflammation. Examples include, but are not limited to, allergic conditions, asthma, allergic rhinitis, inflammatory bowel disease (Crohn's disease and related conditions), multiple sclerosis, chronic obstructive pulmonary disease (COPD), rheumatoid arthritis, and cardiovascular diseases with an inflammatory component.

Allergy is a complex process in which environmental antigens induce clinically adverse reactions.

Asthma can be understood as a basically allergic disease of the lung and its tissues. The asthma inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction.

Hypersensitivity reactions can be local or systemic and typically occur within minutes after allergen exposure in individuals who have previously been sensitized to the respective allergen.

The hypersensitivity reaction of allergy develops when the allergen is recognized by IgE antibodies bound to specific receptors on the surface of effector cells, such as mast cells, basophils, or eosinophils, which cause the activation of the effector cells and the release of mediators that produce the acute signs and symptoms of the reactions. Allergic diseases include asthma, allergic rhinitis (hay fever), atopic dermatitis, and anaphylaxis.

Asthma is thought to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to tissue destruction related to the disorder. Other resident cells, such as smooth muscle cells, lung epithelial cells, mucus-producing cells, and nerve cells may also be abnormal in individuals with asthma and may contribute to its pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually makes asthma a chronic and disabling disorder requiring long-term management.

Chronic obstructive pulmonary (or airways) disease (COPD) is a condition defined physiologically as airflow obstruction that generally results from a mixture of emphysema and peripheral airway obstruction due to chronic bronchitis. Emphysema is characterized by destruction of alveolar walls leading to abnormal enlargement of the air spaces of the lung. Chronic bronchitis is defined clinically as the presence of chronic productive cough for three months in each of two successive years In COPD, airflow obstruction is usually progressive and is only partially reversible. By far the most important risk factor for development of COPD is cigarette smoking, although the disease does also occur in non-smokers.

Chronic inflammation of the airways is a key pathological feature of COPD. The inflammatory cell population comprises increased numbers of macrophages, neutrophils and CD8+ lymphocytes.

Inhaled irritants such as cigarette smoke activate macrophages resident in the respiratory tract as well as epithelial cells leading to release of chemokines (e. g., interleukin-8) and other chemotactic factors which act to increase the neutrophil/monocyte trafficking from the blood into lung tissue, and airways. Neutrophils and monocytes recruited into the airways can release a variety of potentially damaging mediators such as proteolytic enzymes and reactive oxygen species. Matrix degradation and emphysema, with airway wall thickening, surfactant dysfunction and mucus hypersecretion are all potential sequelae of this inflammatory response that lead to impaired airflow and gas exchange.

In both asthma and COPD, although resident cells of the lungs play important parts in disease induction, the movement of inflammatory cells into respiratory tissues can be considered a prerequisite for the late-phase and chronic pathologies of these diseases. Members of the PP2C family of serine/threonine protein phosphotases have recently been shown to be important in the intracellular signalling pathways related to the reorganization of the actin cytoskeleton and cell mobility (Koh et al., Current Biology 12,317-321, 2002).

In patients with active inflammatory bowel disease (IBD), the objective is to achieve clinical remission. For ulcerative colitis (UC), oral or rectal aminosalicylates are widely used, and in more severe flares, corticoids and occasionally cyclosporine. In active Crohn's disease, corticosteroids represent the main treatment; budesonide being one of the most preferred, as this steroid is better tolerated than prednisone.

However, failure to respond, acutely or chronically, to glucocorticoid therapy is a common indication for surgery in IBD, with as many as 50% of patients with Crohn's disease (CD) and approximately 20% of patients with ulcerative colitis (UC) requiring surgery in their lifetime as a result of poor response to glucocorticoids. In clinical practice, patients refractory or intolerant to steroids, immunomodulators such as for example infliximab (Remicade®), can be considered.

Asthma is usually easy to manage and inhaled corticosteroids are the most effective medications currently available to treat symptomatic asthma. However, approximately 5% of asthma patients are not controlled even on high doses of inhaled corticosteroids. Difficult therapy-resistant asthma may be defined as poorly controlled asthma in terms of chronic symptoms, episodic exacerbations, persistent and variable airways obstruction despite the use of high doses of inhaled steroids. Consequently, the disease management of asthma—in particular severe and steroid-resistant asthma—remains a real and daily challenge in the clinic.

Nevertheless, considerable progress has been made in development of drugs for asthma. There have however been few advances in the treatment of other bronchial inflammatory disorders such as chronic obstructive pulmonary disease (COPD). New therapeutic approaches to prevent disease progression are urgently needed, as the inflammatory response in COPD is essentially steroid-resistant.

As with the previously mentioned inflammatory diseases, a proportion of rheumatoid arthritis (RA) patients do not respond adequately to corticosteroids therapy. Likewise, as seen with the other indications, RA patients can be divided on clinical grounds into corticosteroid sensitive (CS) and corticosteroid resistant (CR) subgroups. The underlying mechanism involved in the CS and CR phenomena in patients with RA remain unknown but are of considerable therapeutic interest.

Overall there is an obvious need to address the need of patients that appear unresponsive to conventional steroid therapies or indeed are treatment resistant to a more general spectrum of medications.

Further aims underlying the invention, as well as their associated solutions, will become apparent upon study of the present description, examples and claims.

SUMMARY OF THE INVENTION

The present invention makes available a composition and method for the prevention, treatment and/or alleviation of inflammatory diseases, and in particular inflammatory conditions in the airways of a mammal, as defined in the attached claims, hereby incorporated by reference.

SHORT DESCRIPTION OF THE DRAWINGS

The invention will be disclosed in closer detail in the following description and non-limiting examples, with reference to the drawings in which:

FIG. 1 is a bar diagram, showing the dose response of SEQ. ID. NO. 3 on LPS induced airway inflammation in mice, measured in number of cells ×10E5 in broncho alveolar lavage fluid (BALF);

DESCRIPTION

Figure 1:
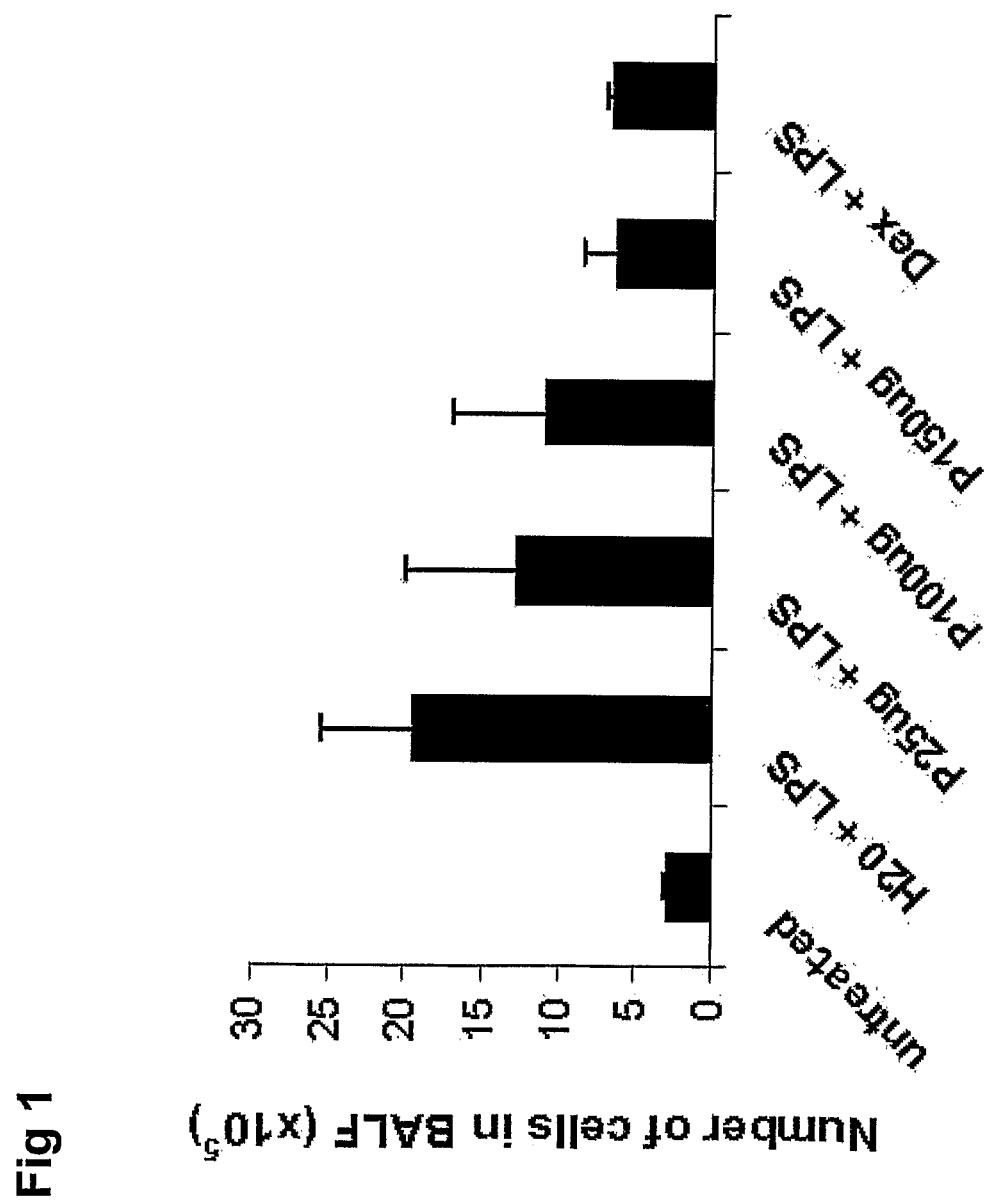

The present inventors have surprisingly found that a CG containing oligonucleotide has the potential to enhance steroid efficacy in the treatment of inflammatory conditions. This is in particular useful in human subjects that fail to demonstrate an adequate response to anti-inflammatory treatments.

The phenomenon of corticosteroid resistance has been most extensively studied in asthmatic patients and to a lesser degree in ulcerative colitis where evidence over the years has accumulated, pointing to a number of cytokine abnormalities.

It may be possible that immunostimulatory oligonucleotides that are able to induce endogenous production of such cytokines such as interferons and IL-10 are able to influence the inflammatory status of steroid resistance or steroid dependent patients in a beneficial manner.

The evidence that certain cytokines can influence the steroid responsiveness is gathered from clinical studies conducted in corticosteroid resistant asthmatics and ulcerative colitis patients who were also all on corticosteroid therapies.

In fact, this type of patient subgroup characteristic was the only common denominator between the clinical studies described below.

Interferons (IFNs) play crucial roles in the regulation of a wide variety of innate and adaptive immune responses. Type I interferons (IFN-alpha/beta) are central to the host defence against pathogens such as viruses, whereas type II interferon (IFN-gamma) mainly contributes to the T-cell-mediated regulation of the immune responses (Taniguchi and Takaoka, 2001). Interferons have also found their place in the successful treatment of various human diseases such as benign neoplastic (Gill et al, 1995) and viral diseases (Niederau et al., 1999; Zeuzem et al., 2000).

In a study (Simon et al, 2003), 10 patients with corticosteroid resistant asthma where administered IFN-alpha ($3 \times 10^6$ IU/day) (Roferon A® Roche) in addition to the prednisone dose they were all receiving. The trial demonstrated high efficacy in these patients and clinical signs of improvement occurring 1-2 weeks after cytokine therapy, allowing the dose of corticosteroids to be reduced. The authors further noted that the IFN-alpha treatment increased the capacity of peripheral blood T cells to produce IFN-gamma, suggesting there had been a shift from a Th2 type response (typical of asthma and allergic diseases) to a Th1 response.

Moreover, the authors showed that there was also an increase in blood T cells secreting IL-10, in those patients that had received cytokine therapy. As corticosteroids mediate their anti-inflammatory effects, in part, by increasing levels of IL-10, the authors conclude that administration of exogenous IFN-alpha broke the corticosteroid resistance in these patients.

Musch et al., (2003) demonstrated a high response rate in corticosteroid refractory ulcerative colitis patients when given INF-beta i.v. The pilot study enrolled 25 severely ill ulcerative colitis patients proving refractory to basic medication. All patients where on corticosteroids at the time of cytokine treatment. Following treatment, 22 of the 25 (88%) went into remission within 3 weeks with a strong decrease in clinical activity index (CAI) noted 1 week after initiating treatment. The mean length of response was 13 months.

In another study, Sumer et al., (1995), reported an 82% improvement rate to s.c. IFN-alpha cytokine treatment in corticosteroid resistant ulcerative colitis patients. They further noted that the 23 patients responded to the cytokine therapy with a fast improvement (within 15 days) and were in complete clinical and endoscopic remission after 6 months of therapy. Three patients entered remission after longer therapy; however, all 26 patients were observed for more than 2 years without receiving additional therapy and remained in full clinical and endoscopic remission during this period.

Another cytokine that has received interest in the pathogenesis of corticosteroid resistance is IL-10. This cytokine is believed to have potent anti-inflammatory effects in that it can suppress the production of pro-inflammatory cytokines. It also has broad implications in the development of certain inflammatory diseases, most noticeably allergy and asthma (Hawrylowicz et al, 2005), as well as playing a central role in the regulation of immune responses. It is believed that corticosteroids exert their anti-inflammatory effects in part by enhancing IL-10 production (Richards et al, 2005).

Numerous clinical studies have indicated that there is a general lack of sufficient levels of IL-10 in asthmatics which may potentially contribute to a more intensive inflammation. In a randomized double-blind clinical study conducted in children with moderate atopic asthma, Stelmach et al., (2002) demonstrated that treatment with Triamcinolone, a corticosteroid, and montelukast, an anti-leukotriene, significantly increased levels of IL-10 in blood serum and in addition significantly improved clinical symptoms.

In another clinical study, levels of IL-10 and IL-10 producing cells were shown to be significantly reduced, in patients with severe persistent asthma when compared to mild asthma (Tomitai et al, 2002). These observations were in agreement with previous findings that there is a defect in the production of cells that are able to produce IL-10 in asthmatic subjects (Tormey et al, 1998).

This defect was also shown to exist in corticosteroid resistant asthmatic patients. Under normal conditions, corticosteroids will cause an increased production of IL-10 in corticosteroid sensitive patients. However, Hawrylowicz et al (2002) could confirm that in corticosteroid resistant asthmatic patients, corticosteroids failed to induce IL-10 synthesis. These observations suggest a strong link between induction of IL-10 synthesis and efficacy of corticosteroids.

In a recently published study (Xystrakis et al., 2006), the authors isolated PBMC from corticosteroid resistant asthmatic patients and could demonstrate that addition of vitamin D3 with dexamethasone to these cultures enhanced IL-10 synthesis to levels observed in cells from corticosteroid sensitive patients cultured with dexamethasone alone. Furthermore, and perhaps most significantly, pre-treatment with IL-10 fully restored IL-10 synthesis in these cells in response to dexamethasone.

The use of human bacterial flora to treat gastrointestinal (GI) disorders is not a novel concept, having been practiced periodically for more than 40 years (Eiseman et al, 1958). Significant clinical improvements have been observed in numerous GI disorders including inflammatory bowel disease (IBD) (Bennet and Brinkman 1989).

In a small study, 6 chronic UC patients who had all previously failed maximum tolerated standard corticosteroid therapies were all given a single faecal enema concomitant to corticosteroid therapies they were currently on. Complete reversal of UC was achieved in all 6 patients following the rectal infusion. The authors also state that all patients ceased anti-inflammatory therapy within 6 weeks and remained in remission in one case for up to 13 years. The apparent success of bacteriotherapy in resistant ulcerative colitis patients may be due to the repopulation of the colon with a "healthy" bacterial flora, but equally as the authors suggest, may also be due to the instillation of a large amount of bacterial DNA, containing abundant CpG motifs, which induced a beneficial immunomodulating effect resulting in complete reversal of the disease (Borody et al., 2003).

A study in asthmatic compared the response to a steroid (prednisone) in both steroid resistant and steroid sensitive patients. The patients were first given a "wash-out" period of one week before administration of the steroid. Cytokine profiles before administration and 1 week after indicated that those patients that responded to the steroid moved from a Th2 type to a more Th1 like status. By contrast, those patients that failed to respond to the administered steroid remained Th2 type (Naseer et al., 1997).

While the reason for steroid resistance in asthmatic patients is not entirely clear, numerous studies in humans have indicated that those patients that are resistant to steroids have high persistent levels of IL-2/4 that are not suppressed by the action of steroids. Furthermore, in vitro studies indicate that steroid insensitive asthma is associated with increased expression of glucocorticoid receptor beta isoform in airway T cells. This isoform, which does not bind glucocorticosteroids, antagonizes the transactivating activity of the classic glucocorticoid receptor. Hence an increased expression of glucocorticoid receptor beta isoform could account for glucocorticoid insensitivity.(Sousa A R et al., 2000; Hamid Q A et al., 1999).

In rheumatoid arthritis a similar scenario has been suggested in that steroid resistant patients demonstrate high levels of IL-4, which cannot be reduced when challenged with steroids (Chikanza et al., 2004).

As used herein, the term "steroid resistant" and "steroid refractory" refers to patients having inflammatory diseases in which administration of steroid treatment, typically effective in patients having such diseases, is ineffective. In this context "steroid resistant" and "steroid refractory" patients include, but are not limited to, patients who do not respond or respond poorly or inadequately as judged by common appropriate physiological parameters to systemic or topical administered steroids. Two types of steroid resistant patients have been described i.e. acquired steroid resistance (Type I) and primary steroid resistance (Type II), both of which are comprised in the present invention (Leung and Szefler et al., 1998).

As used herein, the term "steroid dependence", refers to patients with the inability to be weaned off systemic or topical administered steroid treatment.

A more general picture describing the immunostimulatory activities of polynucleotides are outlined in but are not limited to the following articles: Krieg et al., 1995; Krieg et al.,2006: (2001); Bauer et al., 2002 (2001); Klinman et al. (1999); Jahn-Schmid et al. (1999) and Tighe et al. (2000).

Additional references describing immunostimulatory sequences are provided in but not limited to: Tokunaga et al. (1992); Yamamoto et al. (1992).

For purposes of the invention, the term "oligonucleotide" describes a polynucleoside constructed by linking more than one individual nucleoside unit. Commonly, such oligonucleotides can be obtained from existing nucleic acid sources, including genomic DNA derived from various animal sources, but are more preferably produced by synthetic methods. The nucleoside residues can be coupled to each other by any of the numerous known internucleoside linkages. Such internucleoside linkages include, without limitation the natural internucleoside phosphodiester bond found in natural occurring DNA or indeed modified internucleoside such as but not limited to phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage such as phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

The term "oligonucleotide" includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages A "hybrid oligonucleotide" is an oligonucleotide having more than one type of nucleoside. One preferred example of such a hybrid oligonucleotide comprises a ribonucleotide or 2'-substitutedribonucleotide region and a deoxyribonucleotide region.

For purposes of the invention, the term "immunomodulatory oligonucleotide" refers to an oligonucleotide as described above that induces an immune response either stimulating the immune system or repressing the immune system or both in an organism when administered to a vertebrate, such as a mammal. As used herein, the term "mammal" includes, without limitation rats, mice, cats, dogs, horses, cattle, cows, pigs, rabbits, non-human primates, and humans.

The term "immunomodulatory response" describes the change of an immune response when challenged with an immunomodulatory oligonucleotide. This change is measurable often through the release of certain cytokines such as interferons as well as other physiological parameters such as proliferation. The response can equally be one that serves to stimulate the immune system as well as to repress the immune system depending on the cytokines induced by the immunomodulatory oligonucleotide in question. Equally, the term "immunomodulatory response" could describe a modulation of a subject's response to anti-inflammatory treatment such as steroids.

The phrase "therapeutically effective amount" is used herein to mean an amount sufficient to enhance steroid efficacy or enhance a steroid resistant/dependent subjects response to steroids or other inflammatory agents to some beneficial degree, preferably to enhance by at least about 30 percent, more preferably by at least 50 percent, and even more preferable by at least 90 percent. Most preferably the steroid resistance is reverted to a state of normal responsiveness.

The term "steroid" is used to encompass both corticosteroids and glucocorticosteroids. The term "CG containing oligonucleotide" is used to encompass a oligonucleotide having at least one unmethylated CG dinucleotide within its entire sequence length and being preferably 8 to 100 nucleic acid bases in length.

The expression "enhance steroid efficacy" is here used to encompass a steroid sparing effect, evident as a clinical picture where a simultaneous or sequential treatment with a CG containing immunomodulatory oligonucleotide, preferably a pre-treatment, is shown to reduce the steroid dose necessary to manage the inflammation. The expression "enhance steroid efficacy" is also intended to encompass a synergistic use of a CG containing oligonucleotide and a steroid, either simultaneously or substantially simultaneously, or sequentially or substantially sequentially, shown to reduce the steroid dose necessary to the manage inflammation. The term can also encompass a "re-sensitization" to the inhibitory effects of steroids in a previously known steroid unresponsive/dependent subject. The expressions "steroid resistance" or "steroid refractory" are used to encompass a patient failing to respond adequately to a current therapeutic regime deemed to be normally effective and sufficient to treat the disease in question. The expression "steroid dependent" is used to encompass a patient with an observed inability to be weaned off current therapy without compromising the patient status or increasing the severity of the symptoms of the disease in question.

Preferably, the immunomodulatory oligonucleotide of the invention comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e. g., (Rp)- or (Sp)-phosphorothioate, alkylphosphonate, or phosphotriester linkages) and and aminoalkylphosphoramidates, thionophosphoramidates, thionoalkylphosphonates and thionoalkylphosphotriesters.

According to one embodiment, said substitution may take place at one or more nucleotides independently selected from the final three nucleotides at the 3' terminus and/or 5' terminus of said oligonucleotide. It is also conceived, that the substitution can occur at any position along the entire length of said oligonucleotide, or indeed all intranucleoside linkages are subjected to modification.

In some embodiments, the sugar moiety of the nucleoside can be a non-naturally occurring sugar moiety. For purposes of the present invention, a "naturally occurring sugar moiety" is a sugar moiety that occurs naturally as part of nucleic acid, e. g., ribose and 2'-deoxyribose, and a "non-naturally occurring sugar moiety" is any sugar that does not occur naturally as part of a nucleic acid, but which can be used in the backbone for an oligonucleotide, for example but not limited to hexose. Arabinose and arabinose derivatives are examples of preferred sugar moieties.

Preferred immunostimulatory moieties according to the invention further include nucleosides having sugar modifications, including, without limitation, 2'-substituted pentose sugars including, without limitation,2'-O-methylribose,2'-O-methoxyethyl-ribose, 2'-O-propargylribose, and 2'-deoxy-2'-fluororibose; 3'-substituted pentose sugars, including, without limitation,3'-O-methylribose; 1',2'-dideoxyribose; arabinose; substituted arabinose sugars, including, without limitation,1'-methylarabinose, 3'-hydroxymethylarabinose, 4'-hydroxymethylarabinose, 3'-hydroxyarabinose and 2'-substituted arabinose sugars; hexose sugars, including, without limitation, 1,5-anhydrohexitol; and alpha-anomers.

In another embodiment, preferred immunostimulatory moieties according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some suchfunctionalized alkyl linkers are poly(ethylene glycol) linkers of formula (CH2-CH2-O—), (n=1-9). Some other functionalized alkyl linkers are peptides or amino acids.

In a further embodiment preferred immunostimulatory moieties according to the invention further include DNA isoforms, including, without limitation, -L-deoxyribonucleosides and a-deoxyribonucleosides. Preferred immunostimulatory moieties according to the invention incorporate 3' modifications, and further include nucleosides having unnatural internucleoside linkage positions, including, without limitation, 2'-5', 2'-2', 3'-3' and 5'-5' linkages.

The immunomodulatory oligonucleotide according to the invention comprise at least five oligonucleotides linked via internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages.

Non-covalent linkages include, but are not limited to, electrostatic interaction, hydrophobic interactions,-stacking interactions, and hydrogen bonding. The term "non-nucleotidic linker" is not meant to refer to an internucleoside linkage, as described above, e. g., a phosphodiester, phosphorothioate, or phosphorodithioate functional group that directly connects the 3'-hydroxyl groups of two nucleosides. For purposes of this invention, such a direct 3'-3' linkage (no linker involved) is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

In yet other embodiments, the non-nucleotidic linker is an organic moiety having functional groups that permit attachment to the oligonucleotide. Such attachment preferably is by any stable covalent linkage.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside. In some embodiments, the small molecule linker is glycerol or a glycerol homolog of the general formula HO—(CH2) o-CH(OH)—(CH2) p-OH. [

In a further embodiment the immunomodulatory oligonucleotide of the invention can be modified to adopt a branched-like structure, comprising a branch-point nucleoside to which three core nucleic acid moieties are covalently coupled, where each of the three core nucleic acid moieties are linked to a different position of the branch-point nucleoside. The branch-like modified immunomodulatory oligonucleotide can optionally comprise one or more additional nucleic acid moieties; and at least one nucleic acid moiety comprises the sequence 5'-CG-3'. In an embodiment, one or more of the core nucleic acid moieties in the branch-like modified immunomodulatory oligonucleotide is covalently coupled to the branch-point nucleoside by a linkage that is phosphodiester, phosphotriester, phosphorothioate ester, phosphorodithioate ester, phosphoramidite or alkylphosphonate. In an embodiment, one or more of the three core nucleic acid moieties in the branch-like modified immunomodulatory oligonucleotide is covalently coupled to the branch-point nucleoside through a spacer moiety. Such modifications may impart desired improvements such as cellular uptake and stability, or equally, serve to improve the potency of the immunomodulatory oligonucleotide compound.

In a further embodiment, the immunomodulatory oligonucleotides of the invention can be coupled to a so called "delivery molecule" which imparts a specific cellular uptake or targeting property to the attached immunomodulatory oligonucleotides. Commonly used examples of such include but are not limited to hydrophobic molecules like cholesterol functional groups, specific peptides that have an increased ability to translocate cellular membranes such as cationic antimicrobial peptides or commonly recognized protein transduction domains (PTDs).

In practice, modified or substituted oligonucleotides are often preferred over native forms because of desirable properties such as, for example, enhanced cellular uptake, and increased stability in the presence of nucleases. An oligonucleotide is usually comprised of more than two (2), and typically more than ten (10) and up to one hundred (100) or more deoxyribonucleotides or ribonucelotides, although preferably between about eight (8) and about forty (40), and more preferably between about eight (8) and about twenty (20).

In the inventive method the CG containing immunomodulatory oligonucleotides can be administered by any appropriate administration route, such as, but not limited to, inhalation, ophthalmic, intranasal, parenteral, oral, intradermal and rectal administration. If the patient is also on steroid treatment or other anti-inflammatory treatments such as the use of other immunomodulators, the steroids and immunomodulators can be administered together with the oligonucleotides or separately. The route of administration of the oligonucleotides is independent of the route of administration of steroids.

In one aspect, the invention provides pharmaceutical formulations comprising an immunomodulatory oligonucleotide, according to the invention and a physiologically acceptable carrier. As used herein, the term "physiologically acceptable" refers to a material that does not interfere with the effectiveness of the immunomodulatory oligonucleotide and is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials are described in, e. g., Remington's Pharmaceutical Sciences, 18th Edition, ed. A. Gennaro, Mack Publishing Co., Easton, Pa., 1990.

The present invention also makes available a pharmaceutical composition, wherein said composition comprises a compound or antisense agent as describe above, and a pharmaceutically acceptable formulation and composition, carrier or diluent. Said pharmaceutical composition preferably further comprises a colloidal dispersion system. The pharmaceutical composition of the present invention may be administered in a number of ways depending largely on whether a local, topical or systemic mode of administration is most appropriate for the condition to be treated. These different modes of administration are for example topical (e.g., on the skin), local (including ophthalmic and to various mucous membranes such for example vaginal, nasal, and rectal delivery), oral or parenteral and pulmonary.

The preparation of such compositions and formulations is generally known to those skilled in the pharmaceutical and formulation arts and may be applied to the formulation of the composition of the present invention.

In the scope of this invention, preferred examples of pharmaceutically acceptable salts include but are not limited to (a) salts formed with cations such as sodium, potassium, ammonium, magnesium, calcium, polyamines such as spermine and spermidine, etc. (b) acid addition salts formed with inorganic acids, for example hydrochloric acid, hydrobromic acid, nitric acid, phosphoric acid, sulfuric acid and the like; (c) salts formed with organic acids such as, for example, acetic acid, alginic acid, ascorbic acid, benzoic acid, citric acid, fumaric acid, gluconic acid, maleic acid, methanesulfonic acid, naphthalenedisulfonic acid, naphthalenesulfonic acid, oxalic acid, palmitic acid, polyglutamic acid, p-toluenesulfonic acid, polygalacturonic acid, succinic acid, tartaric acid, tannic acid and the like; and (d) salts formed from elemental anions such as chlorine, bromine, and iodine.

In yet another embodiment, pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavouring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Generally, such carriers should be non-toxic to the recipient at the dosages and concentrations used. Ordinarily, the preparation of such compositions involves combining the therapeutic agent with one or more of the following: buffers, antioxidants, low molecular weight polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are examples of suitable diluents.

The pharmaceutical formulations of the present invention, which may conveniently be presented in unit dosage form, may be prepared according to conventional techniques well known in the pharmaceutical industry.

In yet another embodiment, the compositions of the present invention may be prepared and formulated as emulsions which are typically heterogeneous systems of one liquid dispersed in another in the form of droplets. Examples of naturally occurring emulsifiers used in emulsion formulations include acacia, beeswax, lanolin, lecithin and phosphatides. The application of emulsion formulations via dermatological, oral and parenteral routes and methods for their manufacture have been reviewed in the literature (Gibson, 2001; Carstensen, 1998 ).

In one embodiment of the present invention, the compositions of immunomodulatory oligonucleotides can be formulated as microemulsions. A microemulsion is defined as a system of water, oil and amphiphile which is a single optically isotropic and thermodynamically stable liquid solution.

Another embodiment of the present invention is the use of liposomes for the transfer and delivery of active ingredients to the site of action. Because the liposomal membrane is structurally similar to biological membranes, when liposomes are applied to a tissue, the liposomes start to merge with the cellular membranes. This fact has prompted extensive research in the use of liposomes as potential drug delivery modes.

In another embodiment, the use of penetration enhancers may be of use as a mode of drug delivery. Such agents are classified as belonging to one of five broad categories, i.e., surfactants, fatty acids, bile salts, chelating agents, and non-chelating non-surfactants (Lee et al., 1991). The present invention also relates to a recombinant nucleotide sequence comprising an immunomodulatory oligonucleotide according to the invention. The recombinant immunomodulatory oligonucleotide nucleotide sequence can be inserted in an expression vector, such as a plasmid or virus or any other vector known to a person skilled in the art. Thus, the invention includes the immunomodulatory oligonucleotide sequences operably linked to one or more expression control elements, such that in vivo or in vitro expression of said immunomodulatory oligonucleotide could be achieved. The vector capable of harbouring said antisense oligonucleotides can be of eukaryotic or prokaryotic origin.

The concentration of an immunomodulating oligonucleotide in a pharmaceutically acceptable mixture will vary depending on several factors, including the dosage of the compound to be administered, the pharmacokinetic characteristics of the compound(s) employed, the age, sex and condition of the patient, as well as the route of administration. Effective amounts of immunomodulating oligonucleotides for enhancing steroid efficacy in a steroid resistant or steroid dependent patient would broadly range between about 0.01 μg to about 100 mg per kg of body weight, preferably about 0.1 μg to about 10 mg, and most preferably about 1 μg to about 5 mg per kg of body weight of a recipient mammal.

In certain preferred embodiments, immunomodulatory oligonucleotide, according to the invention are administered in combination with but not limited to, anti-inflammatory agents such as TNF-anti-bodies, non-steroidal anti-inflammatory drugs (NSAIDs) such as ibuprofen, naproxen aspirin and other salicylates and cox-2 inhibitors, such as celecoxib (Celebrex), corticosteroids (inhaled, oral, rectal), mast cell stabilizers, and the leukotriene modifier drugs.

According to another embodiment, said steroid resistant/dependent patient is currently on anti-inflammatory treatment, such as protein-based immunomodulators. The immunomodulators may be selected from the group consisting of anti-inflammatory agents, leucotriene antagonists, IL-4 muteins, soluble IL-4 receptors, immunosuppressants, anti-IL-4 antibodies, IL-4 antagonists, anti-IL-5 antibodies, soluble IL-1 3 receptor-Fc fusion proteins, anti-IL-9 antibodies, CCR3 antagonists, CCR5 antagonists, VLA-4 inhibitors, down regulators of IgE, and anti-TNF-alpha antibodies and other versions thereof.

According to another embodiment, said patient is currently on non-steroidal anti-inflammatory agents. Presently available non-steroidal anti-inflammatory agents include but are not limited to Piroxicam, Mefenamic acid, Nabumetone, Sulindac, Tolmetin, Ketorolac, Rofecoxib, Diclofenac, Naproxen, Flurbiprofen, Celecoxib, Oxaprozin, Diflunisal, Etodolac, Fenoprofen, Ibuprofen, Indomethacin, Ketoprofen, Etodolac, and Meloxicam.

According to a further embodiment of the invention, the treatment comprises the administration of anti-histamines, or anti-histamines and prostaglandin inducers. According to one embodiment, the anti-histamine is selected from the group consisting of loratidine, cetirizine, buclizine, ceterizine analogues, fexofenadine, terfenadine, desloratadine, norastemizole, epinastine, ebastine, astemizole, levocabastine, azelastine, tranilast, terfenadine, mizolastine, and betatastine.

For purposes of this aspect of the invention, the term "in combination with" means in the course of treating the same disease in the same patient, and includes administering the immunomodulatory oligonucleotide may occur in any order, including simultaneous administration, as well as temporally spaced order of up to several months apart. Such combination treatment may also include more than a single administration of the immunomodulatory oligonucleotide. More preferable the immunomodulatory oligonucleotide of the invention is given to a steroid resistant or steroid dependent patient after that patient has started steroid therapy, and is on a stable dosing regime.

Experimental data indicate that a CG containing immunomodulatory oligonucleotide may modulate the immune system, resulting in an improvement or reversal of the inflammation, or in an improved response to the steroids, or a re-sensitization of the patient to the anti-inflammatory effects of steroids.

In accordance therewith, the present invention makes available a method for enhancing steroid efficacy in the treatment of a patient afflicted with an inflammatory condition, wherein an oligonucleotide having the sequence

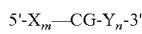

$$5'\text{-}X_m\text{---}CG\text{-}Y_n\text{-}3'$$

is administered in an effective amount to said patient and wherein X is A, T, C or G, Y is A, T, C, or G, m=1-40, n=1-40 and wherein at least one CG dinucleotide is unmethylated.

In the above general formula, m is an integer in the interval 1-40, preferably 1-30, preferably 1-20, more preferably 1-12, more preferably 1-10, more preferably 1-8, more preferably 1-6, more preferably 1-4, more preferably 1-2.

Similarly, n is an integer in the interval 1-40, preferably 1-30, preferably 1-20, more preferably 1-12, more preferably 1-10, more preferably 1-8, more preferably 1-6, more preferably 1-4, more preferably 1-2.

According to a particularly preferred embodiment, the oligonucleotide is symmetrical in relation to the central CG motif, that is n is equal to m, and both being integers preferably in the interval 1-40, more preferably 1-30, more preferably 1-20, more preferably 1-12, more preferably 1-8, more preferably 1-6, more preferably 1-4, and more preferably 1-2.

It is also conceived that an oligonucleotide according to the invention comprises two or more CG motifs, in tandem or in any position along the entire length of the oligonucleotide.

As defined above, the inventive method concerns the use of a CG oligonucleotide to improve the responsiveness of a patients, or as a steroid sparing agent. One embodiment thereof is the treatment of a patient afflicted with an inflammatory condition, wherein said patient is steroid dependent and currently on steroid treatment. Another embodiment thereof is the treatment of a patient afflicted with an inflammatory condition, wherein said patient is defined as being steroid resistant or refractory and currently on steroid treatment.

According to another embodiment, said patient is currently on anti-inflammatory treatment, preferably steroid treatment.

According to a preferred embodiment, the inflammatory condition is an inflammatory condition of the airways, more preferably an inflammatory condition chosen among Addison's disease, adult respiratory distress syndrome (ARDS), chronic obstructive pulmonary disease (COPD), allergy, and asthma. Most preferably, the inflammatory condition is asthma.

In the method according to the present invention, the oligonucleotide is administered in combination with steroids, meaning simultaneously, substantially simultaneously, sequentially or substantially sequentially.

The present invention also comprises the use of an oligonucleotide having the Sequence

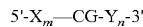

$5'\text{-}X_m\text{—}CG\text{-}Y_n\text{-}3'$ for the manufacture of a medicament for enhancing steroid efficacy in the treatment of a patient afflicted with an inflammatory condition, wherein X is A, T, C or G, Y is A, T, C or G; m=1-40, n=1-40 and wherein at least one CG dinucleotide is unmethylated.

In the above general formula, m is an integer 1-40, preferably 1-30, preferably 1-20, more preferably 1-12, more preferably 1-10, more preferably 1-8, more preferably 1-6, more preferably 1-4, more preferably 1-2.

Similarly, n is an integer 1-40, preferably 1-30, preferably 1-20, preferably 1-20, more preferably 1-12, more preferably 1-10, more preferably 1-8, more preferably 1-6, more preferably 1-4, more preferably 1-2.

According to a particularly preferred embodiment, the oligonucleotide is symmetrical in relation to the central CG motif, that is n is equal to m, and both are preferably integers in the interval 1-40, more preferably 1-30, more preferably 1-20, more preferably 1-12, more preferably 1-8, more preferably 1-6, more preferably 1-4, and more preferably 1-2.

It is also conceived that an oligonucleotide according to the invention comprises two or more CG motifs, in tandem or in any position along the entire length of the oligonucleotide.

As defined above, the inventive method concerns the use of a CG containing oligonucleotide having at least one unmethylated CG dinucleotide within its entire sequence to enhance the effect of steroids, or as a steroid-sparing agent. One embodiment thereof is the treatment of a patient afflicted with an inflammatory condition, wherein said patient is steroid dependent and currently on steroid treatment and wherein the CG containing oligonucleotide having at least one unmethylated CG dinucleotide is administered concomitantly with the steroid.

Another embodiment thereof is the treatment of a patient afflicted with an inflammatory condition, wherein said patient is defined as being steroid resistant or refractory and currently on steroid treatment and wherein the CG containing oligonucleotide having at least one unmethylated CG dinucleotide is administered concomitantly to the steroid. A non-limiting list of steroids, presently available, includes prednisone, methyl-prednisolone, beclomethasone, fluticasone, tramcinolone, budesonide, and dexamethasone, According to another embodiment, said steroid resistant/dependent patient is currently on anti-inflammatory treatment, preferably steroid treatment.

According to a further embodiment, said patient is preferably in a remission state of inflammatory disease activity and is administered a therapeutic dose of CG containing oligonucleotide having at least one unmethylated CG dinucleotide within its entire sequence in a prophylactic regime, such that in the event of a relapse, the severity of the inflammatory disease is reduced.

According to a further embodiment, said steroid resistant/dependent patient is preferably in a active state of inflammatory disease activity and is administered a therapeutic dose of CG containing oligonucleotide having at least one unmethylated CG dinucleotide within its entire sequence, concomitant to other widely used anti-inflammatory based therapies, such that the efficacy of the anti-inflammatory treatment is increased resulting in an improved status of the disease.

According to a preferred embodiment, the inflammatory condition is an inflammatory condition of the airways, more preferably an inflammatory condition chosen among Addison's disease, adult respiratory distress syndrome, chronic obstructive pulmonary disease (COPD), allergy, and asthma.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Pharmaceutical compositions, which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the responsible physician, in light of factors related to the subject that requires treatment. Such factors, which can be taken into account, include the severity of the disease state, general health of the subject, age, weight, and gender of the subject, diet, time and frequency of administration, drug combination(s), reaction sensitivities, and tolerance/response to therapy. Dosage and administration are adjusted to provide sufficient levels of the active ingredient or to maintain the desired effect. Long-acting pharmaceutical compositions can be administered every 3 to 4 days, every week, or once every two weeks depending on the half-life and clearance rate of the particular formulation.

Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Steroid resistance or dependence is still a major clinical concern for a large number of patients afflicted with inflammatory diseases as current therapies rely on the use of potent immunomodulators that can induce serious side-effects. A simple straightforward method to enhance steroid efficacy in a steroid unresponsive individual with little risk of unwanted side-effects would essentially improve anti-inflammatory treatment, thus ameliorating the disease in question, and increasing the quality and length of life for a large number of patients.

EXAMPLES

Example 1

Comparison of Different Oli-Godeoxynucleotides (ODN)

In the studies that follow, five different oligonucleotides were used for in vitro stimulation experiments using human peripheral blood mononuclear cells (PBMCs), mouse spleenocytes and in vivo studies in an LPS asthma induced murine model. All oligonucleotides were ordered from Biomers, Ulm/Donau, Germany.

TABLE 1

CpG-containing ODNs

| | | |
|---|---|---|
| SEQ. ID. NO 1 | 5'-G*G*A*ACAGTTCGTCCAT*G*G*C-3'<br>(Hu p65)AS | |
| SEQ. ID. NO 2 | 5'-G*G*A*ACAGTTGCTCCAT*G*G*C-3'<br>(Hu p65 rev)AS | |
| SEQ. ID. NO 3 | 5'-G*A*A*ACAGATCGTCCAT*G*G*T-3'<br>(Mu p65)AS | |
| SEQ: ID: NO 4 | 5'-G*A*A*ACAGATGCTCCAT*G*G*T-3'<br>(Mu p65 rev)AS | |
| SEQ. ID. NO 5 | 5'-A*G*C*TGAGTAGCCTATA*G*A*C-3'<br>(negative control) | |
| SEQ. ID. NO 6 | 5'-G*G*T GCA TCG ATG CAG*G*G*G*<br>G*G-3'<br>(human positive control) | |
| SEQ. ID. NO 7 | 5'-T*C*C*A*T*G*A*C*G*T*T*C*C*T*G*<br>A*C*G*T*T-3'<br>(murine CpG positive control) | |
| SEQ. ID. NO 8 | 5'-T*C*G*T*C*G*T*T*T*T*G*T*C*G*T*<br>T*T*T*G*T*C*G*T*T-3'<br>(human positive control) | |

In all cases a "*" marked base indicates a phosphorothioate linkage, while non marked bases indicate phosphodiester linkage.

It should be noted that SEQ.ID.NO 6, SEQ.ID.NO 7 and SEQ.ID.NO 8 are publicly available sequences, described as oligonucleotides having a strong interferon inducing potential. They therefore serve as positive controls for the immunomodulatory ability of the CG dinucleotide containing oligonucleotides SEQ.ID.NO 1 and SEQ.ID.NO 3.

SEQ.ID.NO 2 and SEQ.ID.NO 4 are identical to SEQ.ID.NO 1 and SEQ.ID.NO 3 respectively, with one deliberate difference. The internal CG dinucleotides in both SEQ.ID.NO 1 and SEQ.ID.NO 3 have been reversed to GC with the aim of abolishing the immunostimulatory capacity while remaining as close to the original compound as possible. SEQ.ID.NO 2 and SEQ.ID.NO 4 therefore function as appropriate negative controls for SEQ.ID.NO 1 and SEQ.ID.NO 3 respectively.

The lyophilized oligonucleotides were delivered as a lyophilized powder and first diluted in a small volume of distilled water to form a stock solution. After thorough mixing, each oligonucleotide was further diluted in a series of different dilutions. The OD A260/A280 was determined for each dilution using SmartSpec 3000, BioRad). The average concentration of all readings, for all dilutions, was calculated in order to determine the stock concentration. The stock solutions were stored at −20° C. and repeated thawing/freezing was avoided.

For all oligonucleotides, a portion of the concentrated stock solution was diluted further, in order to obtain one high and one low concentration stock solution (1 µg/µl). The concentration was determined by measuring OD using a spectrophotometer as mentioned above.

The working concentrations used in the experiments; 0,1 µM, 1 µM, 5 µM, 10 µM, 25 µM, 50 µM, 100 µM, 150 µM and 200 µM were prepared by diluting the different oligonucleotides further in medium using the high stock solution (usually 20 µg/µl) and the low stock solution (1 µg/ul). The dilutions made to give rise to each of the required final concentrations needed depended on the number of wells to be treated (i.e. final volume) and differed from experiment to experiment.

Example 2

First Animal Study

The general aim of this study was to examine the pharmacological effects of an experimental oligonucleotide SEQ. ID. NO. 3, as a potential immunomodulating compound. The aim of the study was to examine the pharmaceutical effects of SEQ. ID. NO. 3 using airway inflammation as disease endpoint, and to compare the efficacy with that of corticosteroids.

Materials and Methods

Animals

C57BL/6 mice were purchased from Bomholtgaard, Ry, Denmark. Animals were fed with standard chow and water ad libitum and allowed to acclimatize for at least 7 days in an accredited animal facility before use. In all experiments female mice of ages between 9-11 weeks were used. All experiments were approved by the local ethical committee for animal experiments in Umeå, Sweden.

Induction of Acute Lung Inflammation

Bacterial endotoxin, LPS (*Escherichia coli* 0128:B12, Sigma, St. Louis, Mo.) was administered to anaesthetised mice (enflurane) by tracheal instillation in a total volume of 50 µl in a concentration of 5 µg. Control mice were given solvent alone (endotoxin-free distilled water). Through previous experiments the optimum concentration of LPS was determined to be 5 µg.

Analysis of Leukocytes in Bronchoalveolar Fluid

The mice were sacrificed by cervical dislocation 20 h after LPS instillation and their tracheae was cannulated with polyethylene tubing. Bronchoalveolar 20 lavage (BAL) was performed using 1-ml aliquots of ice-cold Hanks balanced salt solution to a recovered volume of 4 ml. Total number of leucocytes in bronchoalveolar lavage fluid (BALF) was counted using a Bürker chamber and trypan blue solution. Differential cell counts were determined on duplicate cytocentrifuged preparations stained with May-Grünewald Gemisa. Three 25 hundred cells were counted from each slide and the percentage of neutrophils determined.

Treatment of LPS-Induced Lung Inflammation with SEQ.ID.NO 3 or Dexamethasone

Mice were treated with an experimental oligonucleotide (SEQ.ID.NO 3, in concentrations of 25 µg, 100 µg or 150 µg.

The oligonucleotide was administered by tracheal instillation to anaesthetised mice in a total volume of 50 µl 18 h prior to instillation of 5 µg LPS. Control mice received 50 µl endotoxin-free distilled water.

To compare the effect of the oligonucleotide to conventional treatment with anti-inflammatory corticosteroids, one group of mice received dexamethasone (Sigma St Louis, Mo.). Dexamethasone (10 mg/kg body weight) dissolved in PBS was 6(12) injected intraperitoneally (i.p) into mice 1 h prior LPS exposure. Withdrawal and analysis of bronchoalveolar lavage fluid (BALF) was performed 20 h after challenge.

Statistical Analysis

The results are expressed as mean+standard error of the mean (SEM). Statistical analysis was performed using Students t-test (two-tailed). Data were considered to be statistically significantly different when the p value was less than 0.05. Statistical analyses were performed only when the number of animals in each group was ≥4.

Results Corresponding to Example 2

Effect of Oligonucleotide SEQ.ID.NO 3 on LPS-Induced Airway Inflammation

The oligonucleotide was administered intratracheally 18 h prior to LPS instillation and the effect on the neutrophilic response was studied by withdrawal and analysis of BALF 20 h after LPS challenge. The corticosteroid dexamethasone was included in the experiment to compare the effect of SEQ.ID.NO 3 with that of conventional anti-inflammatory treatment.

Figure 2:
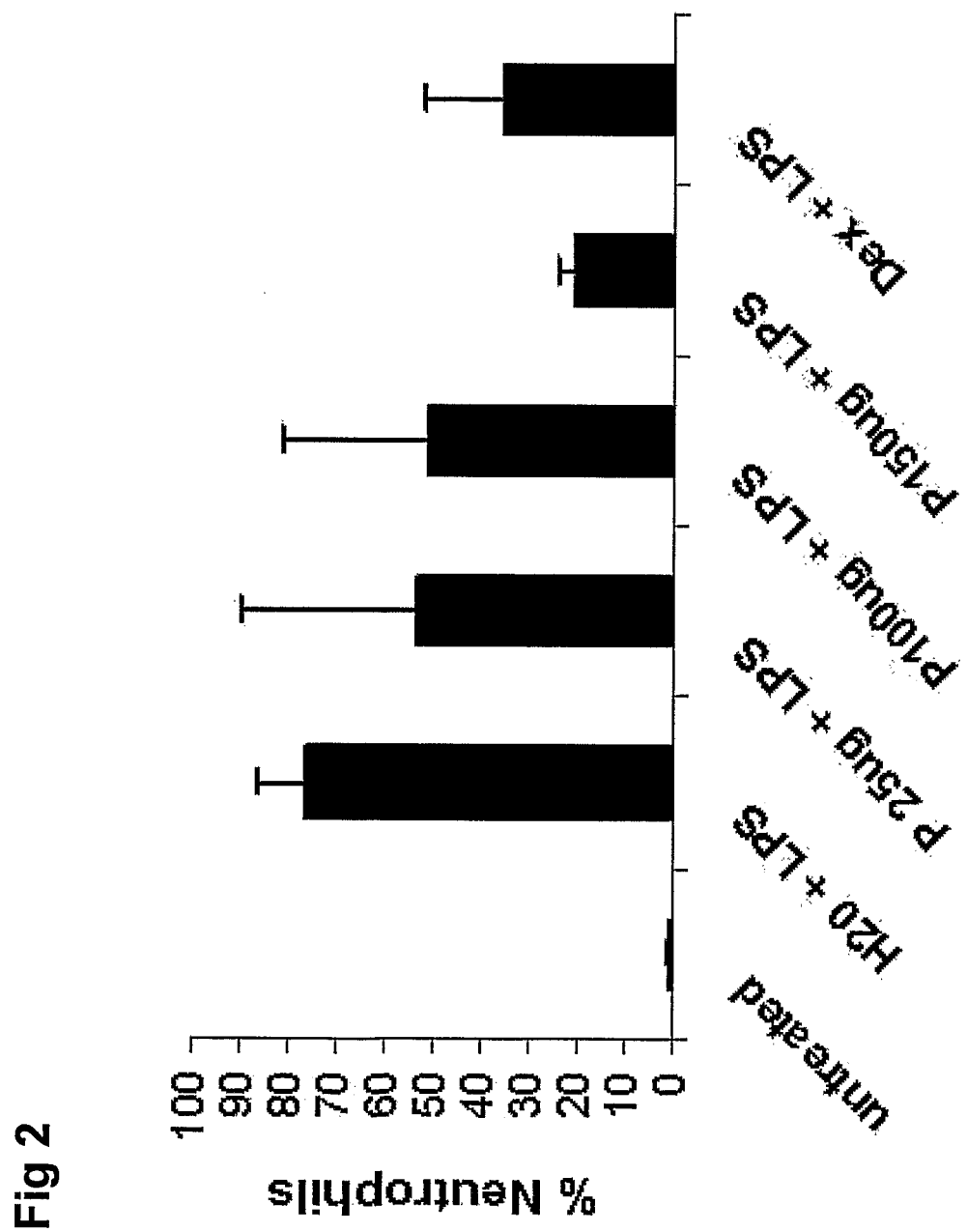
FIG. 2 is a bar diagram as above, where the response is measured in % neutrophils.

Administration of SEQ.ID.NO 3 resulted in a dose-dependent reduction of neutrophils in BALF (FIG. 1). In animals treated with 150 µg SEQ.ID.NO 3, a more than 50% reduction in the number of recovered neutrophils in BAL was observed (FIG. 2). This anti-inflammatory effect was at least as powerful as high-dose treatment with dexamethasone.

Conclusions

In the present study, the inventors used a mouse model of neutrophilic lung inflammation induced by tracheally instilled endotoxin. In this model, the inhibition of the inflammatory response by airway administered SEQ.ID.NO 3 was studied. Surprisingly, the experiments showed that pre-treatment with SEQ.ID.NO 3 results in significantly reduced neutrophilic response in the airways.

Example 3

Second LPS Induced Asthma Study

As with example 2, aim of the study was to examine the pharmaceutical effects of SEQ. ID. NO. 3 using airway inflammation as disease endpoint, and to compare the efficacy with that of corticosteroids. This study included larger numbers of animals per group to increases statistical significance. The induction of LPS induced asthma and the protocol of analyses was conducted as described in example 2.

Briefly, mice were treated with an SEQ.ID.NO 3 (150 µg/animal) administered by tracheal instillation 18 h prior to challenge with 5 µg LPS. One group of mice represented healthy untreated individuals. Control mice were given solvent only ($H_2O$) and LPS. One group received dexamethasone (5 mg/kg) one hour before LPS instillation and one group were given a combination treatment. Analysis of BALF was performed 20 hours after the last treatment. Total number of cells in BALF and number of neutrophils is shown. Data is expressed as mean±SD. *=p<0.001 and =p<0.01, in treated groups vs the control group (one-way ANOVA and Bonferroni post hoc test). Calculations were performed by SPSS software (12.0). n=6 in all groups.

Results Corresponding to Example 3

Effect of Oligonucleotide SEQ.ID.NO 3 on LPS-Induced Airway Inflammation

Figure 3:
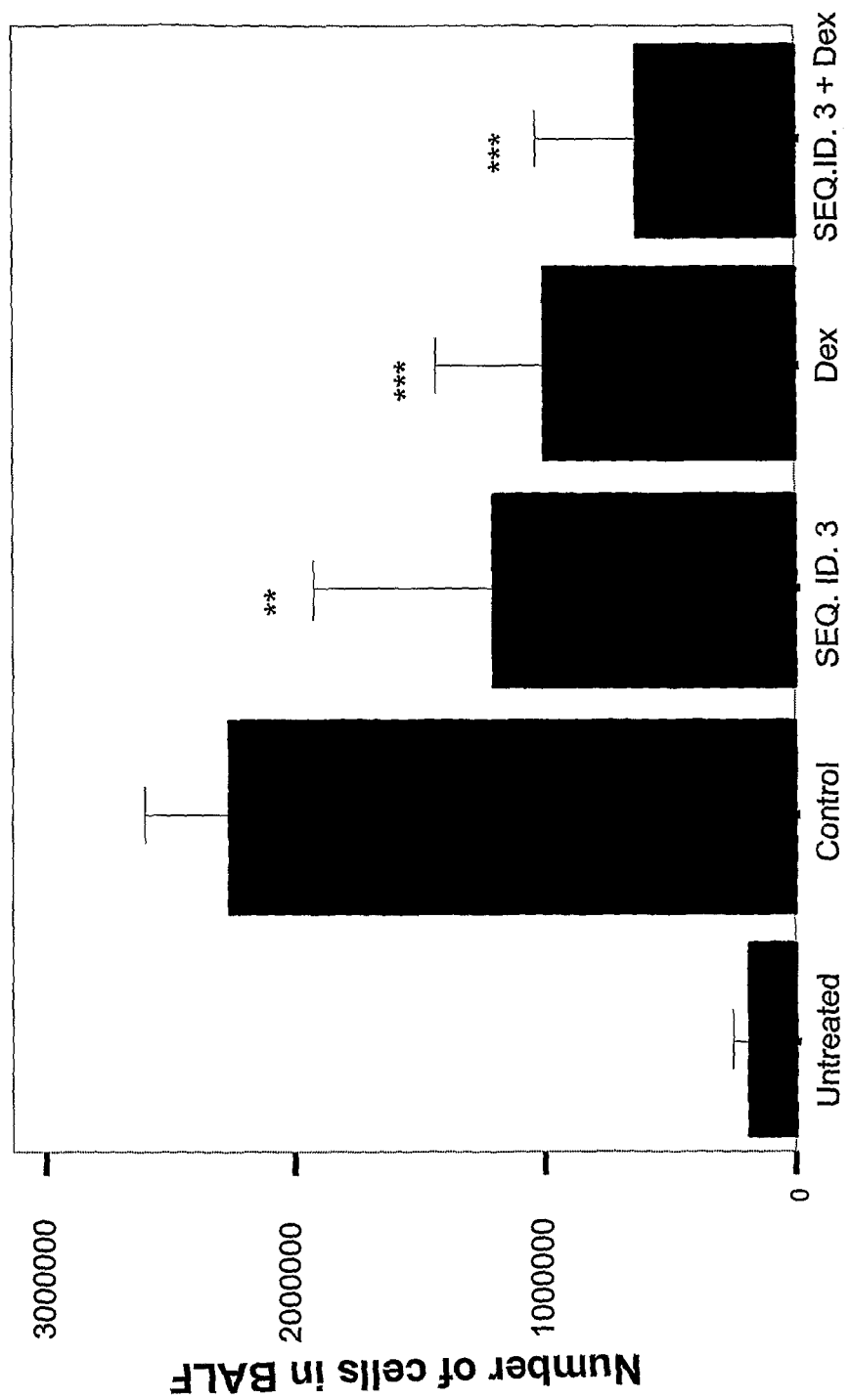
FIG. 3 is a bar diagram illustrating the inhibition of inflammatory responses on an LPS induced murine asthma model following treatment with SEQ.ID.NO 3 and dexamethasone, measured as BALF cell number.

The effect of SEQ.ID.NO 3 and dexamethasone treatment on the totally number of infiltrating cells into the BAL fluid can be seen in FIG. 3. A single dose of 150 ug of SEQ.ID.NO 3 resulted in a reduction in BAL fluid cell number of approximately 50% verses control (p=0.005), which was somewhat more pronounced for dexamethasone (p=0.0001). Surprisingly the combination of both SEQ.ID.NO 3 and dexamethasone produced a level of inhibition greater than that achieved by either mono-therapy alone.

Figure 4:
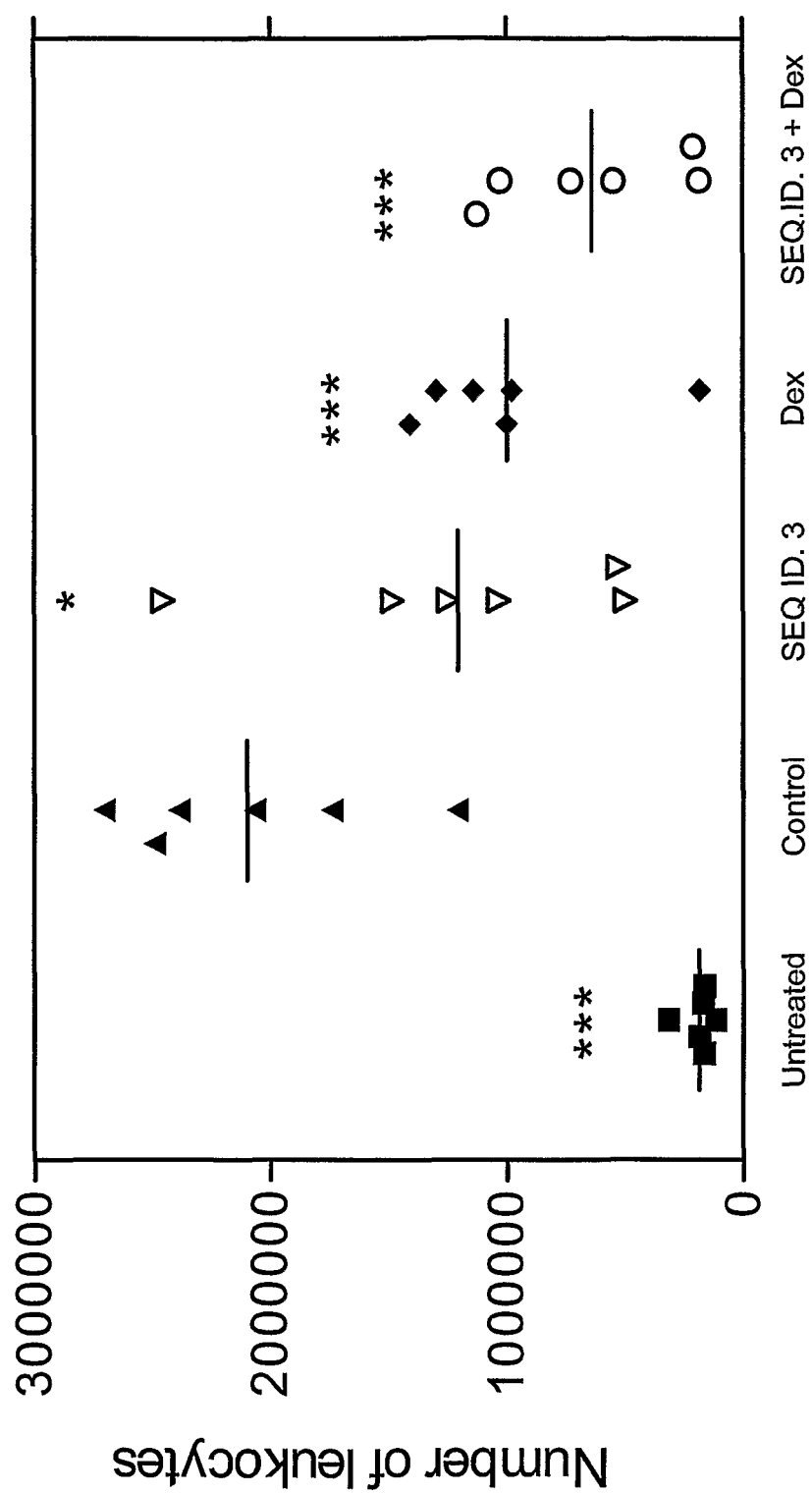
FIG. 4 is a chart showing the inhibition of influx of leukocytes in BALF following treatment with SEQ.ID.NO 3 and dexamethasone.

By determination of cells within the BAL fluid, the largest proportion are neutrophils and leukocytes. FIG. 4 shows the total number of leukocytes in BAL fluid 20 h after LPS instillation for all data points. Each point represents one animal and as seen in FIG. 3, the combination of both SEQ.ID.NO 3 and dexamethasone achieved the highest degree of inhibition of leukocytes. ***p<0.001, *p<0.05, using One-way ANOVA with Dunnett's post hoc corrections versus control group (GraphPad).

Figure 5:
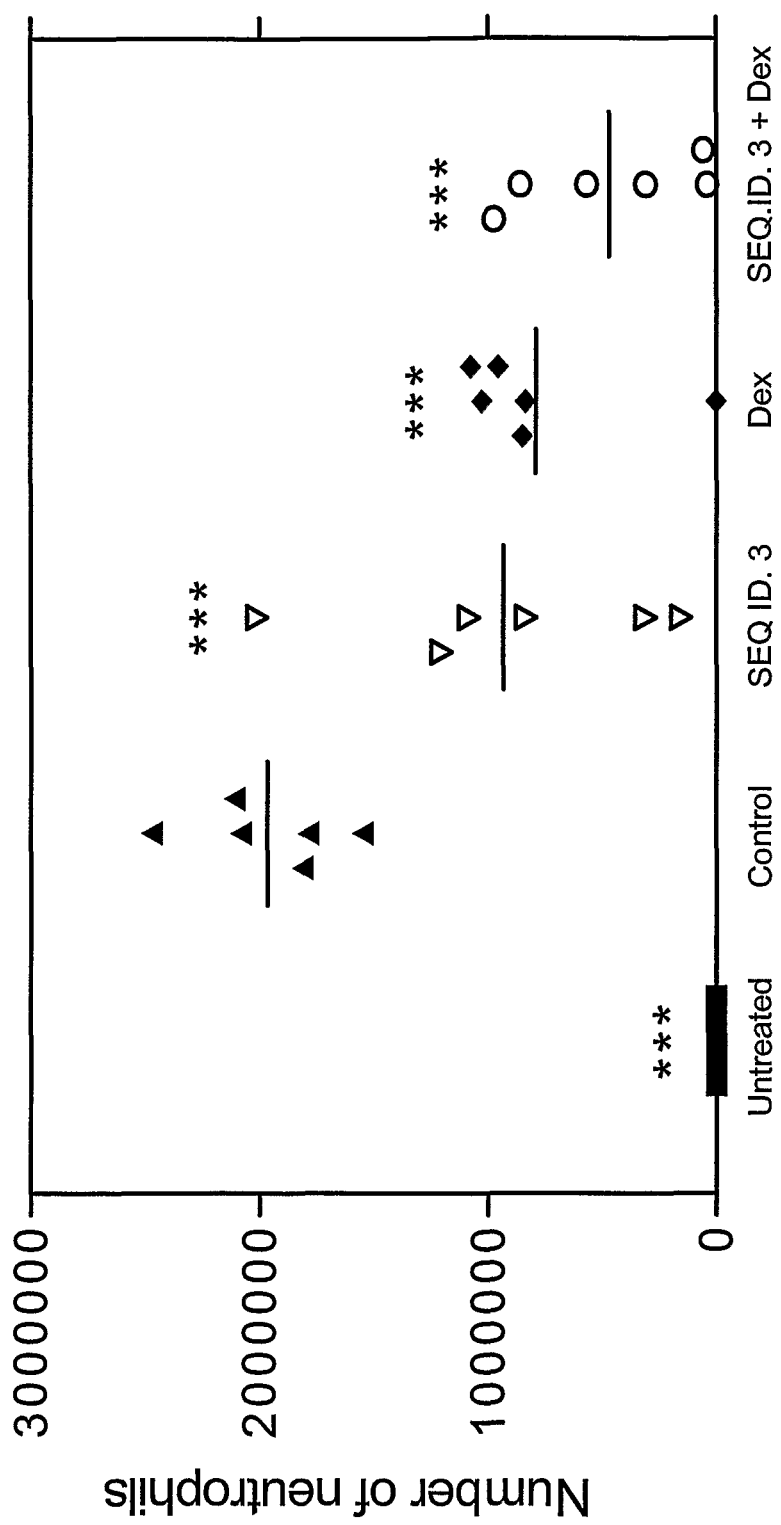
FIG. 5 shows the inhibition of influx of neutrophils in BALF following treatment with SEQ.ID.NO 3 and dexamethasone.

FIG. 5 is a graph, showing the effect of SEQ.ID.NO 3 treatment on neutrophil influx. Each data point represents a single observation, i.e., a single mouse. As before, the combination of both SEQ.ID.NO 3 and dexamethasone achieved the highest degree of inhibition. ***p<0.001, using One-way ANOVA with Dunnett's post hoc corrections versus control group (GraphPad).

Example 4

Third LPS Induced Asthma Study

As with examples 1 and 2, aim of the study was to examine the pharmaceutical effects of SEQ. ID. NO. 3 using airway inflammation as disease endpoint, and to compare the efficacy with that of corticosteroids. In addition, a number of control oligonucleotides were included being SEQ.ID.NO 4, and SEQ.ID.NO 7. The induction of LPS induced asthma and the protocol of analyses was conducted as described in Example 2.

Briefly, LPS-induced airway inflammation in mice was treated with SEQ.ID.NOs 3, 4 and 7 (150 µg/animal) administered by tracheal instillation 18 h prior to challenge with 5 µg LPS. The untreated group represents healthy individuals and mice in the control group were given solvent only ($H_2O$+ LPS). The control treatment of dexamethasone (5 mg/kg, i.p.) was given one hour before LPS instillation. Analysis of BAL fluid was performed 20 hours after LPS instillation. The total number of leukocytes and neutrophils in BAL fluid is shown. Data expressed as mean±SD (n=6). ***p<0.001, *p<0.05, using One-way ANOVA with Dunnett's post hoc corrections versus control group.

Results Corresponding to Example 4

Figure 6:
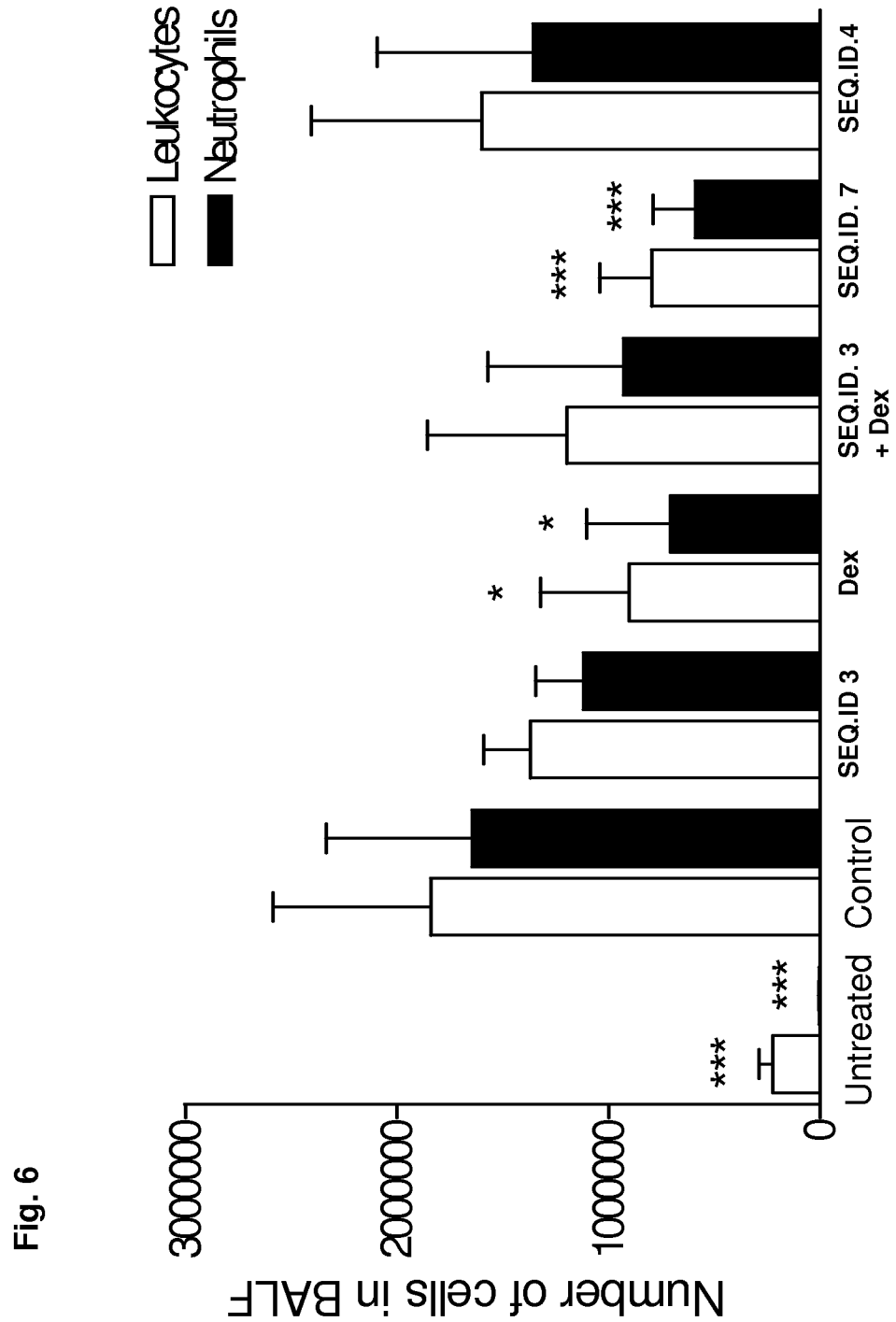
FIG. 6 is a bar diagram illustrating the inhibition of inflammatory responses on LPS induced murine asthma model following treatment with SEQ.ID.NO 3 SEQ.ID.NO 4, SEQ.ID.NO 7 and dexamethasone as measured by BALF cell number.

Effect of Oligonucleotides SEQ.ID.NOs 3, 4 and 7 on LPS-Induced Airway Inflammation FIG. 6 makes evident a clear induction in the number of BAL fluid cells following LPS challenge seen in the control group. Those mice receiving SEQ.ID.NO 3, as illustrated in the previous two examples, show reduced numbers of infiltrating inflammatory cells in the BAL fluid. Mice receiving SEQ.ID.NO 7 show a more dramatic level of inhibition being as effective as dexamethasone. Clearly those mice receiving SEQ.ID.NO 4 show little effect as would be expected due to the absence of any CG dinucleotide within the sequence of SEQ.ID.NO 4. The combination of both dexamethasone and SEQ.ID.NO 3 has not demonstrated the potential increase of effect as seen in Example 2.

Figure 7:
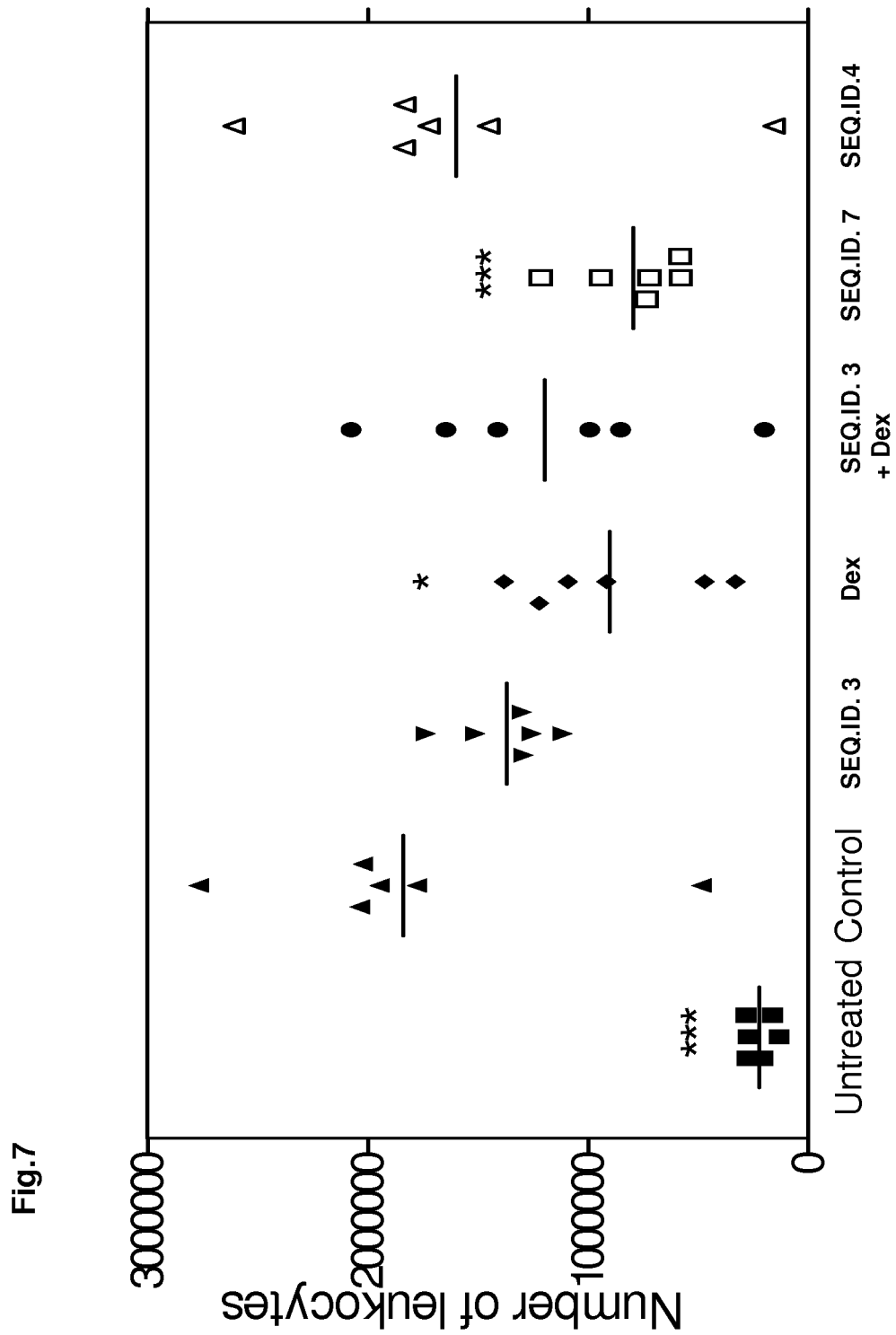
FIG. 7 is a chart showing the inhibition of influx of leukocytes in BALF following treatment with SEQ.ID.NO 3 SEQ.ID.NO 4, SEQ.ID.NO 7 and dexamethasone as measured by BALF cell number.

FIG. 7 depicts the same results as indicated in FIG. 6 whereby each data point represents a single animal. Here it is more obvious to note that the negative control oligonucleotide SEQ.ID.NO 4 shows no effect when compared to the control group. Data expressed as mean±SD (n=6). ***p<0.001, * p<0.05, using One-way ANOVA with Dunnett's post hoc corrections versus control group. Note: If the non-responding individual in the control group is excluded, all other groups (except those receiving SEQ.ID.NO 4) display a significantly reduced inflammatory response (*p<0.05 for SEQ.ID.NO 3 and p<0.001 for the other groups).

Figure 8:
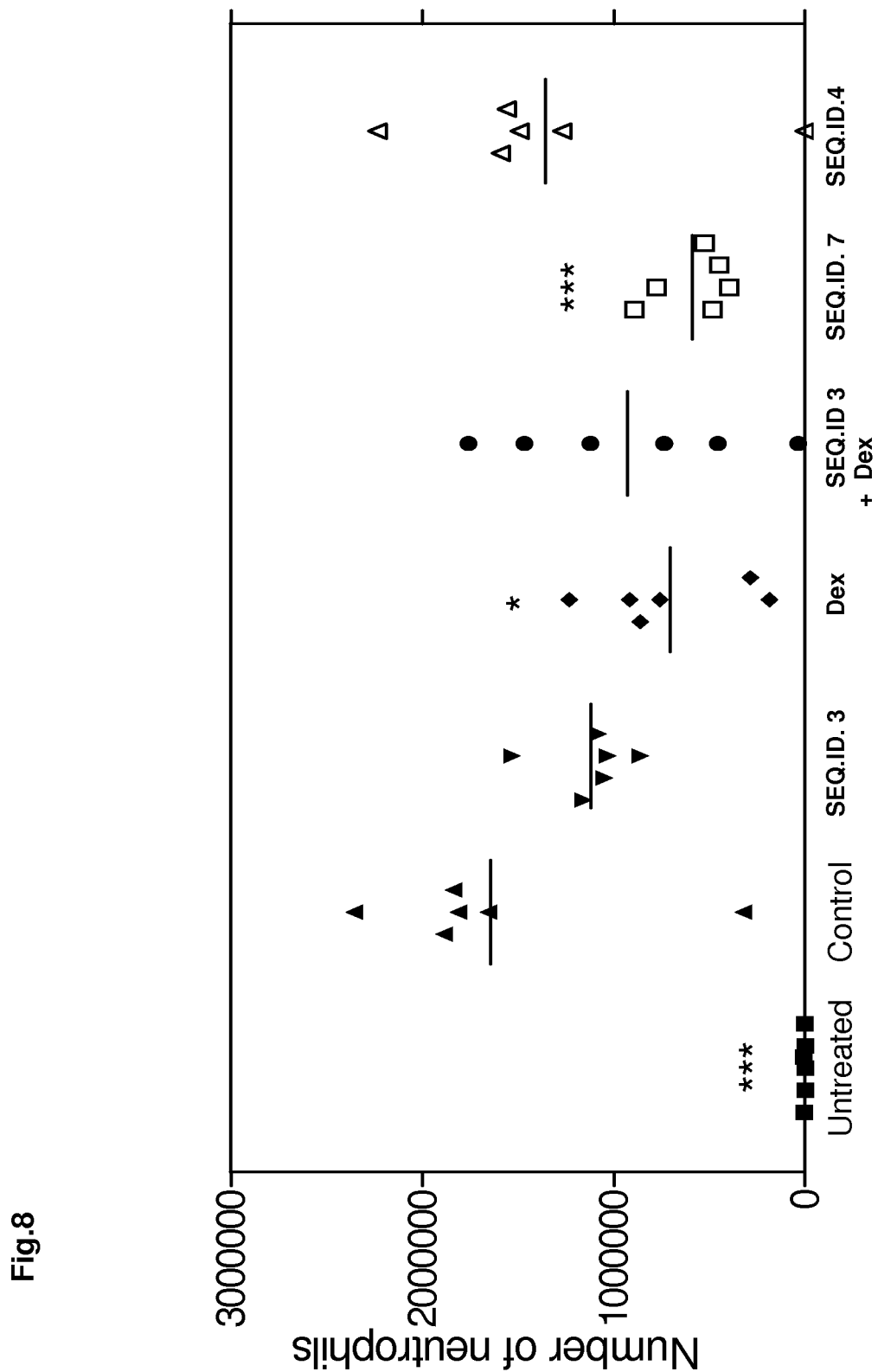
FIG. 8 shows the inhibition of influx of neutrophils in BALF following treatment with SEQ.ID.NO 3, SEQ.ID.NO 4, and SEQ.ID.NO 7 and dexamethasone as measured by BALF cell number.

FIG. 8 likewise, depicts the same results as indicated in FIG. 6 whereby each data point represents a single animal. Here again it is more obvious to note that the negative control oligonucleotide SEQ.ID.NO 4 shows no effect when compared to the control group. Data expressed as mean±SD(n=6). ***p<0.001, * p<0.05, using One-way ANOVA with Dunnett's post hoc corrections versus control group. Note: If the non-responding individual in the control group is excluded, all other groups (except those receiving SEQ.ID.NO 4) display a significantly reduced inflammatory response (*p<0.05 for SEQ.ID.NO 3 and ***p<0.001 for the other groups).

Example 5

Preparation of a Single Cell Suspension from Murine Spleen

The spleen was excised from a test animal. A single cell suspension was prepared using a nylon cell strainer (100 µm). The cells were washed once in complete RPMI medium at 1200 rpm for 7-10 minutes, whereupon the supernatant was poured off and the cells resuspended. 1 ml of "red blood cell lysing buffer" was added, and the mixture incubated for 1-2 minutes at RT. 5 ml of complete RPMI was added and the mixture centrifuged as above (C2).

The supernatant was poured off, the pellet resuspended and another 5 ml of complete RPML added. The cells were counted by dilution in trypan blue, so that between 50-100 cells were counted in the area.

Approximately 500,000 mouse splenocyte cells per well were incubated for 48 hours in the presence of the different oligonucleotides at the concentrations indicated. Specifically, SEQ.ID.NO 3, SEQ.ID.NO 4, and SEQ.ID.NO 7. Following incubation the wells were developed according to the kit suppliers recommendations and the average number of positive spots per well were determined using a AID ELISpot reader system, (Strassberg Germany).

Results corresponding to Example 5
Effect of Oligonucleotides SEQ.ID.NOs 3 4 and 7 on Murine Spleen Cells Induction of IL-10

Figure 9:
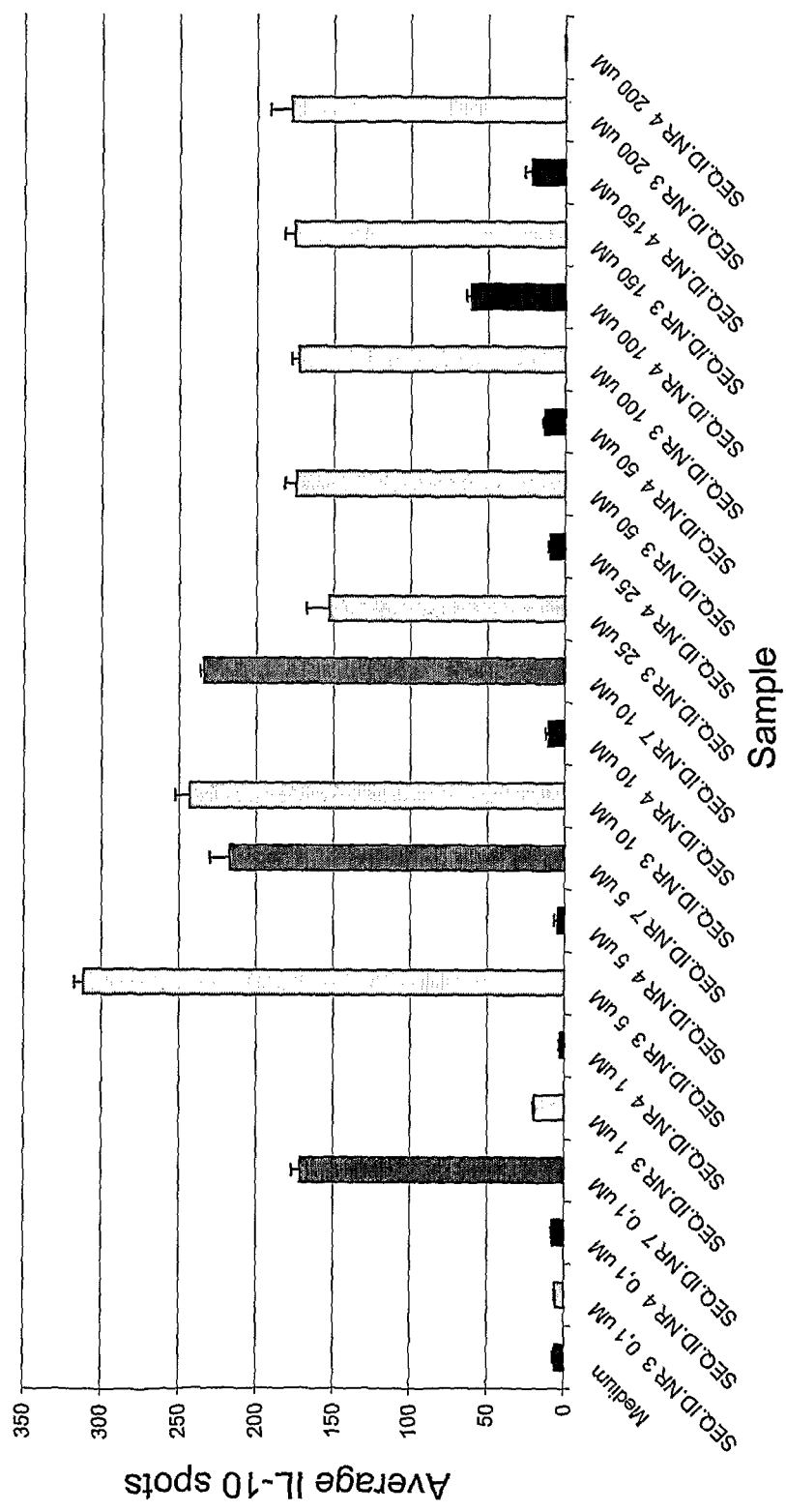
FIG. 9 is a bar diagram showing the induction of IL-10 from murine spleen cells following treatment with increasing amounts of SEQ.ID.NO 3, SEQ.ID.NO 4, and SEQ.ID.NO 7.

FIG. 9 shows the results obtained, and from the graph it is clearly apparent that both SEQ.ID.NO 3 and SEQ.ID.NO 7 (positive control) induce significant levels of IL-10, where as the negative control SEQ.ID.NO 4, shows no induction of this cytokine. Whereas SEQ.ID.NO 7 induces IL-10 at as a concentration of 0.1 uM, SEQ.ID.NO 3 first induces significant number of positive IL-10 producing cells at 5 uM, indeed, SEQ.ID.NO 3 appears to be more potent at this effect that SEQ.ID.NO 7 for the same concentration. As expected, by removing the CG dinucleotide pair present in SEQ.ID.NO 3, (i.e., control SEQ.ID.NO 4) the effect of inducing IL-10 it's abolished. Hence it is clear that SEQ.ID.NO 3 is able to induce the production of IL-10 in mouse splenocytes. Medium indicates wells that received no oligonucleotide and thereby represent spontaneous background levels of IL-10.

Results Corresponding to Example 5
Effect of Oligonucleotides SEQ.ID.NOs 3, 4 and 7 on Murine Spleen Cells: Induction of IFN-Gamma Regarding the production of IFN-gamma, mouse splenocytes were treated as described above, with the intention to monitor levels of IFN-gamma by Elispot asssy. Identical conditions and concentrations of oligonucleotides where used.

Figure 10:
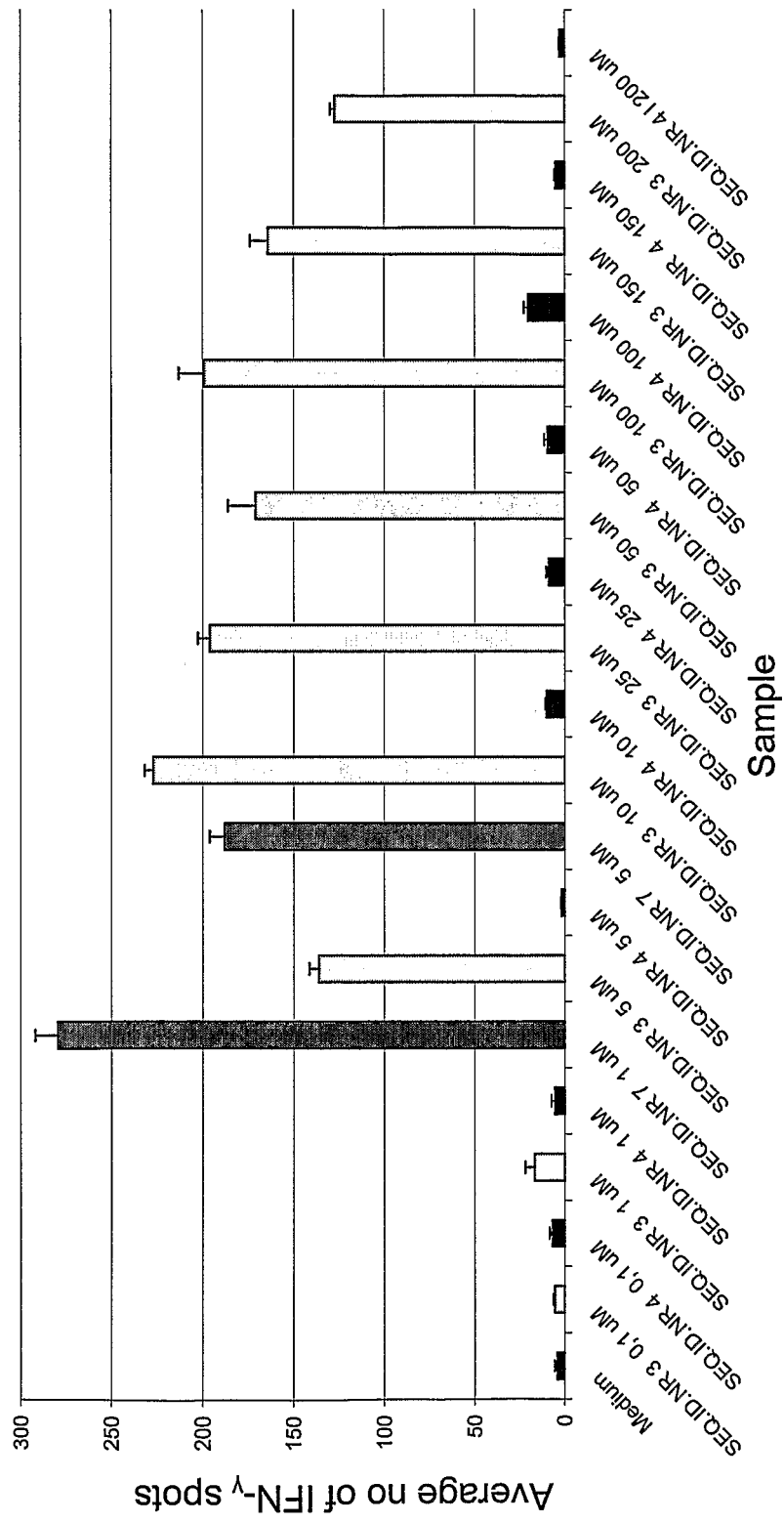
FIG. 10 illustrates the induction of IFN-gamma from murine spleen cells following treatment with increasing amounts of SEQ.ID.NO 3, SEQ.ID.NO 4, and SEQ.ID.NO 7.

From FIG. 10 it is clear that only those oligonucleotide sequences containing at least one CG dinucleotide (e.g SEQ.ID.No 3 and SEQ.ID.NO 7) motif within their totally sequence length where capable of inducing significant levels of IFN-gamma when compared to medium alone. The negative control oligonucleotide SEQ.ID.NO 4 showed no such inducing potential as expected. The column marked medium indicates those levels representing spontaneous positive IFN-gamma producing cells.

Example 6

Preparation of Peripheral Blood Mononuclear Cells (PBMC)

Materials

Whole blood was obtained from healthy blood donors. PBMCs were prepared from 30 ml whole blood according to the following protocol:

30 ml blood was transferred directly into heparinized tubes. All blood was transferred into one 50 ml Falcon tube and PBS added up to 50 ml. 15 ml Ficoll (17-1440-03, obtained from Amersham Bioscience AB, Uppsala) was then added into two falcon tubes (50 ml). The PBS-treated blood was then carefully added on the top of to Ficoll, 25 ml to each tube. The tubes were then centrifuged 25 min at 1700 RPM at RT (20° C.).

RPMIc medium was prepared under sterile conditions, using a 0.22 uM filter. (RPMIc denotes a RPMI 1640 culture medium (R0883, Sigma) supplemented with 5% heat-inactivated (56° C.,1 h) FCS 1.5 mM L-glutamine (G7513, Sigma), 100 U/ml penicillin and 100 ug/ml streptomycin, PEST (P0781, Sigma), hepes (H0887, Sigma), and gentamycin (G1272, Sigma)).

The interphase was carefully pipetted from the two tubes into 2x 50mi Falcon tubes. PBS was added up to 50 ml in each tube, and the tubes centrifuged for 10 min at 1700 RPM (4° C.).

The supernatant was discarded, and PBS added to 30 ml, whereupon the tubes were centrifuged at 10 min at 1500 RPM (4° C.). Again, the supernatant was discarded, 10 ml PBS added, and the pellets from the two falcon tubes pooled.

The cells were counted and left in PBS, then centrifuged at 1200 RPM, 10 min. Medium was then added to obtain the concentration of interest, and the cells counted (16 squares)× 3. The mean value was calculated and multiplied with the dilution factor×$10^4$=cells/ml. Diluting the cells to 10 million/ ml will result in 500.000 cells/50 ul medium, 6 million/ml will be 300.000/50 ul medium.

Example 7

Elispot Assay

Elispot assays where performed according to the manufactures recommended guidelines (MabTech) and the plates

Example 8

ELISA Assay

ELISA assays where performed according to the manufactures recommended guidelines (R&D systems). Plates were analyzed using AID ELISpot reader system (Autoimmun Diagnostika GmbH, Strassberg Germany).

Example 9

Induction of Cytokine IL-10 from Healthy Human PBMC in Response to ODN Treatment Approximately 500,000 PBMC cells per well, derived from blood from healthy human donors, were incubated for 48 hours in the presence of the different oligonucleotides. Specifically, SEQ.ID.NO 1, SEQ.ID.NO 2, SEQ.ID.NO 6 and SEQ.ID.NO 8. Following incubation, the wells were developed according to the kit supplier's recommendations and the average number of positive cells producing IL-10 per well were counted using an AID ELISpot reader system, (Autoimmun Diagnostika GmbH, Strassberg, Germany).
Results Corresponding to Example 9
Effect of Oligonucleotides SEQ.ID.NOs 1 2 6 and 8 on Human PBMC Induction of IL-10

Figure 11:
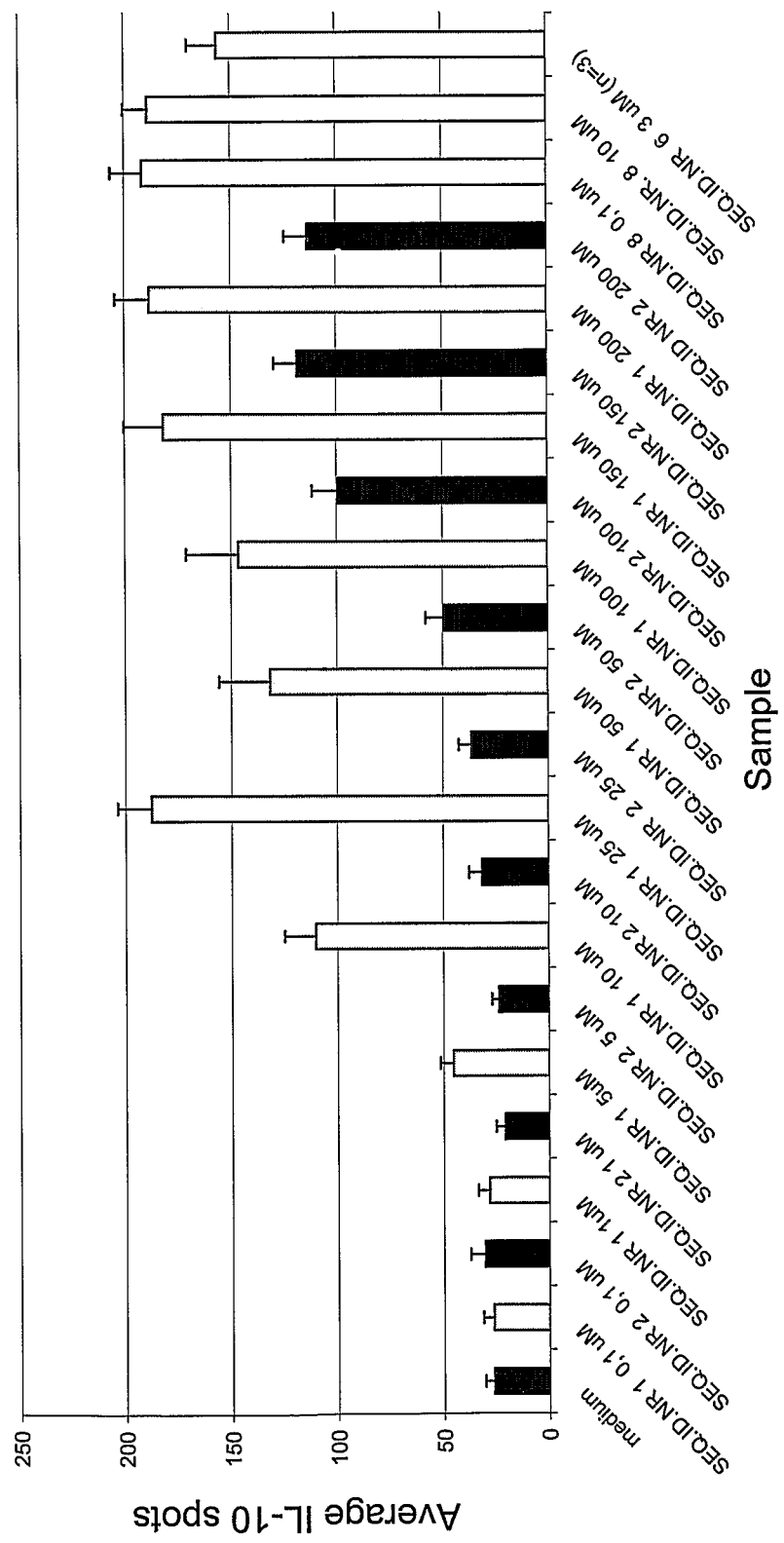
FIG. 11 shows the average levels of IL-10 induction from human peripheral blood mononuclear cells (PBMC) following 48 hours incubation with increasing amounts of SEQ.ID.NO 1, SEQ.ID.NO 2, SEQ.ID.NO 6 and SEQ.ID.NO 8.

FIG. 11 is a histogram indicating the average number of positive IL-10 producing human PBMC from 5 healthy individuals when incubated for 48 hours with the oligonucleotides SEQ.ID.NO 1, SEQ.ID.NO 2, SEQ.ID.NO 6 and SEQ.ID.NO 8 at the concentrations indicated. As anticipated, the negative control oligonucleotide SEQ.ID.NO 2 failed to induce IL-10, until very high concentrations of around 100 uM where reached. SEQ.ID.NO 6 and SEQ.ID.NO 8 served as positive controls and show a strong potential to induce IL-10. Incubation of PMBCs with SEQ.ID.NO 1 showed a clear potential to induce IL-10 producing cells at a concentration starting from around 5uM and continued up to the highest concentration used 200 uM. The column marked medium indicates those levels representing spontaneous positive IL-10 producing cells. The results are the average taken from 5 different individuals (bars indicate SEM)

Example 10

Induction of IFN-Gamma from Healthy Human PBMC in Response to ODN Treatment

Figure 12:
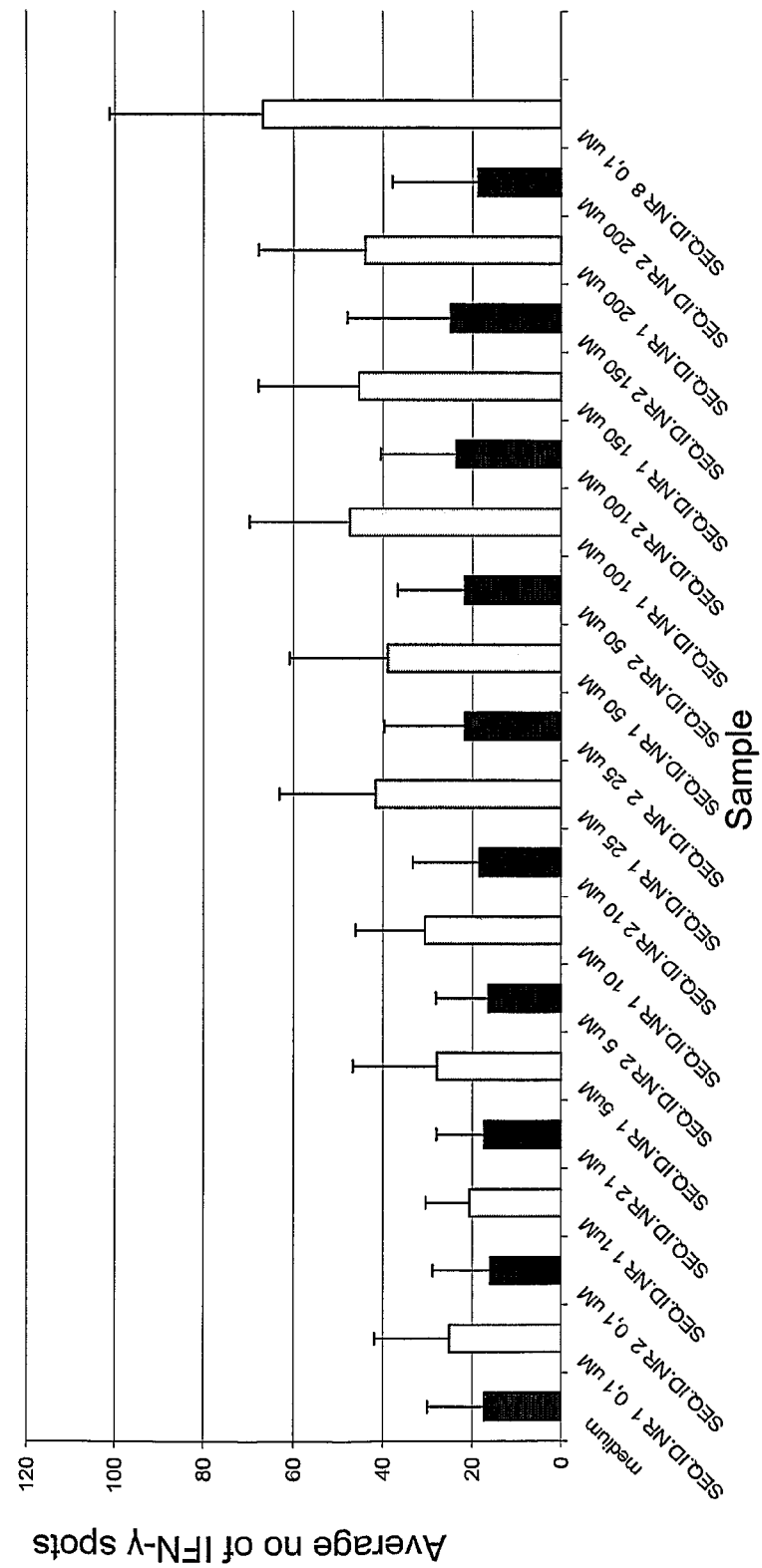
FIG. 12 shows the average levels of IFN-gamma induction from human PBMC following 48 hours incubation with increasing amounts of SEQ.ID.NO 1, SEQ.ID.NO 2, and SEQ.ID.NO 8.

Approximately 500,000 PBMC cells per well, derived from healthy human blood were incubated for 48 hours in the presence of the different oligonucleotides. Specifically, SEQ.ID.NO 1, SEQ.ID.NO 2, and SEQ.ID.NO 8. Following incubation, the wells were developed according to the kit suppliers recommendations and the average number of positive cells producing IFN-gamma per well were counted using a AID ELISpot reader system.
Results Corresponding to Example 10
Effect of Oligonucleotides SEQ.ID.NOs 1 2. and 8 on Human PBMC Induction of IFN-Gamma The histogram depicted in FIG. 12 indicates the number of positive IFN-gamma producing human PBMC from 7 healthy individuals when incubated for 48 hours with the oligonucleotides SEQ.ID.NO 1, SEQ.ID.NO 2, and SEQ.ID.NO 8 at the concentrations indicated. Here the induction of IFN-gamma becomes apparent at a concentration of around 25 uM, and remains high right up to the highest concentration of 200 uM. The background level is not exceeded by the negative control The column marked "medium" indicates those levels representing spontaneous positive IFN-gamma producing cells. The results are the average taken from 7 different individuals (bars indicate SEM).

Example 11

Induction of IFN-Alpha from Healthy Human PBMC in Response to ODN Treatment

Figure 13:
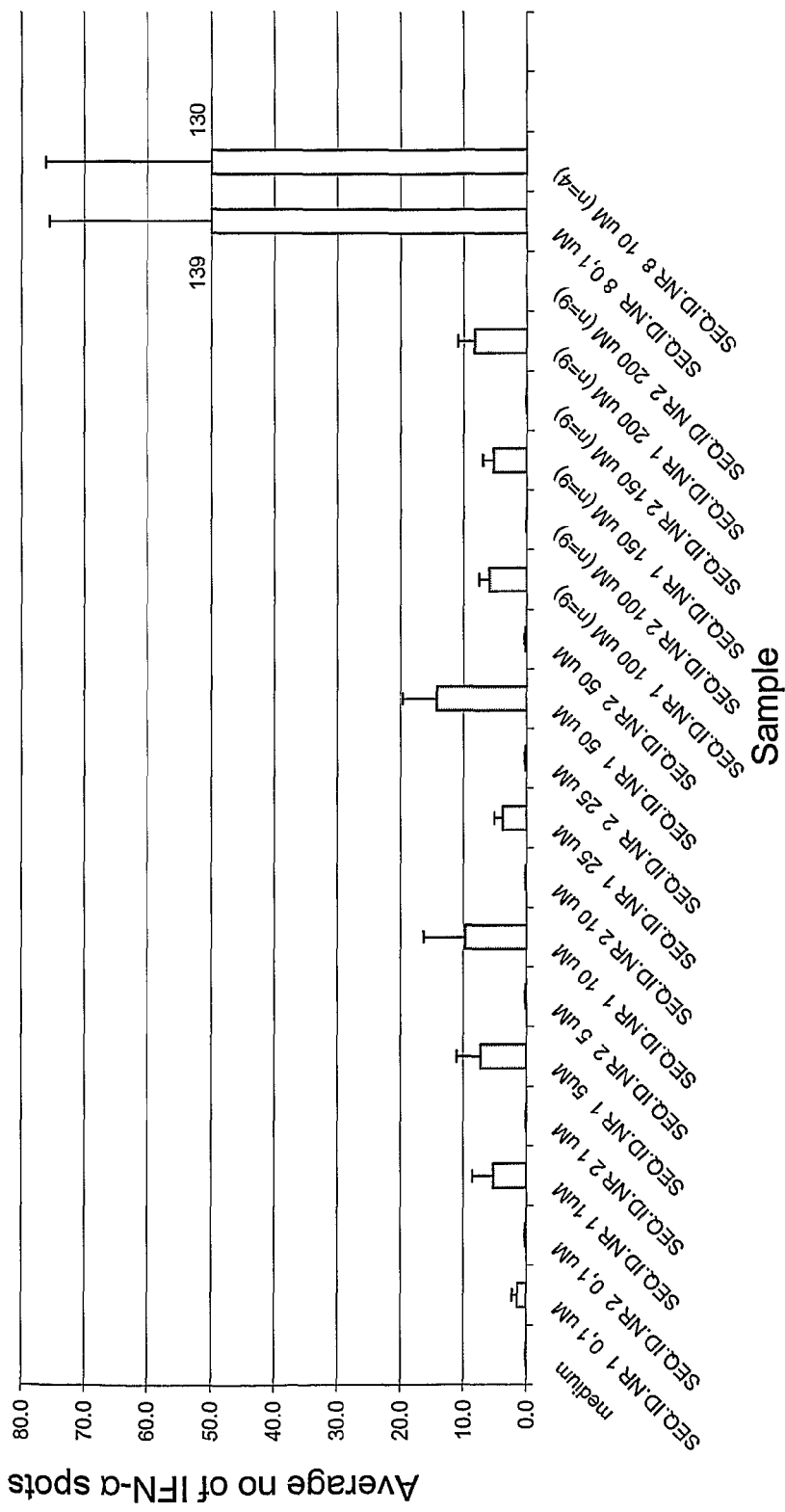
FIG. 13 shows the average levels of IFN-alpha induction from human PBMC following 48 hours incubation with increasing amounts of SEQ.ID.NO 1, SEQ.ID.NO 2, and SEQ.ID.NO 8.

For this assay again 500,000 PBMC cells per well, derived from healthy human blood were incubated for 48 hours in the presence of the different oligonucleotides. Specifically, SEQ.ID.NO 1, SEQ.ID.NO 2, and SEQ.ID.NO 8. Following incubation, the wells were developed according to the kit suppliers recommendations and the average number of positive cells producing IFN-alpha per well were determined using an AID ELISpot reader.
Results Corresponding to Example 11
Effect of Oligonucleotides SEQ.ID.NOs 1, 2, and 8 on Human PBMC Induction of IFN-Alpha FIG. 13 indicates the results obtained, from 10 healthy individuals. SEQ.ID.N0 1 demonstrated a clear inducing potential as seen by the large increase in number of cells producing IFN-alpha starting at a concentration of 1 uM and continuing with little further increase to 200 uM. The positive control oligonucleotide SEQ.ID.NO 8 likewise shows a strong potential to induce IFN-alpha being apparent already at a concentration of 0.1 uM. Further more, the negative control oligonucleotide SEQ.ID.NO 2 again fails to induce any measurable levels of IFN-alpha.

The results in summary indicate that both SEQ.ID.NO 1 and SEQ ID.NO 3 both act as immunomodulating oligonucleotides in human and mouse cells respectively. This is confirmed by the production of interferons (specifically IFN-alpha and IFN-gamma), which are according to literature hall mark cytokines indicative of a immunostimulatory effect due to CG dinucleotides within the sequences.

Example 12

Potential Synergy of IL-10 Induction from Healthy Human PBMC in Response to SEQ.ID.NO 1 Treatment with Steroid For this assay again 500,000 PBMC cells per well, derived from blood from healthy human donors, were incubated for 12 hours in the presence of various concentrations of dexamethasone, after which, the cells were washed and fresh medium as added. The cells were then allowed to further incubate in the presence of either 25 uM or 100 uM of SEQ.ID.NO 1 for an additional 24 hours after which levels of IL-10 were measured using a commercial available IL-10 ELISA kit.

Figure 14:
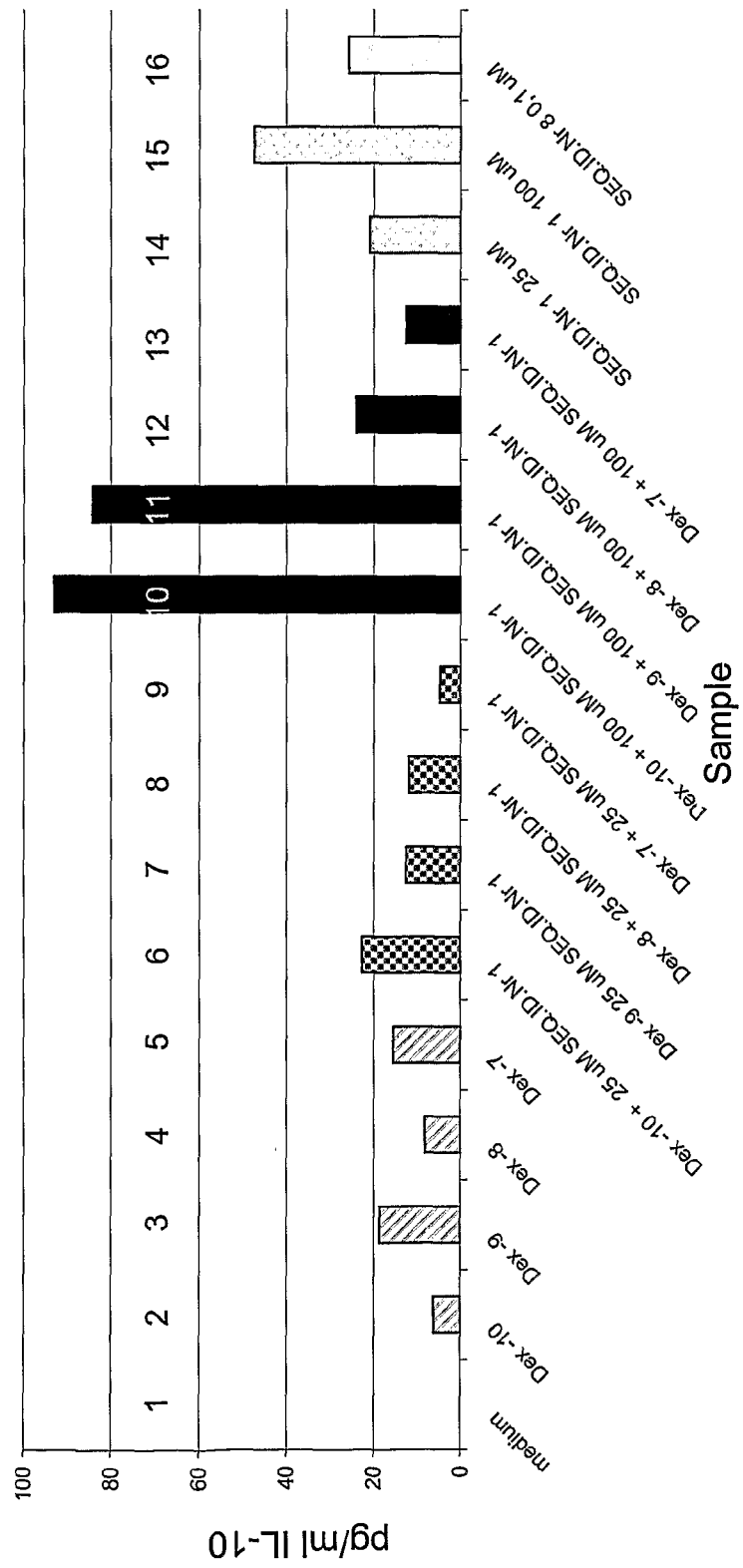
FIG. 14 shows the concentration of IL-10 from human PBMCs in response to incubation with SEQ.ID.NO 1, 24 hours with or without prior incubation with dexamethasone.

As seen in FIG. 14, the results indicate that little IL-10 production is seen from cells given a dexamethasone pulse for 12 hours and incubated in medium alone for a further 24 hours (see bars 2-5). Cells given 25 uM of SEQ.ID.NO 1 after prior incubation with dexamethasone also show little production of IL-10 (see bars 6-9). However, upon increasing the concentration of SEQ.ID.NO 1 to 100 uM, there was a dramatic increase in the amount of IL-10 produced (see bars 10 and 11) being most apparent for those conditions where the pre-incubation with dexamethasone was at a concentration of $10^{-10}$ M (100 pM). Bars 14 and 15 represent levels of IL-10 produced by SEQ.ID.NO 1 in the absence of pre-steroid incubation.

It was surprising that the combination of a prior treatment of dexamethasone followed by incubation with SEQ.ID.NO 1 produced levels higher than either mono treatment alone, and suggests there is a potential synergistic effect between steroid and an oligonucleotide containing an active CG dinucleotide. The anti-inflammatory effects of steroids are in part attributed to their ability to induce IL-10.

This observation has implications regarding the possibility to reduce the effective dose of a steroid required when treating a disorder in a human such that the risk of unwanted effects are further reduced. Furthermore, the immunomodulatory oligonucleotide may serve to re-sensitize a patient's response to steroid therapies.

Example 13

The Immunostimulatory Effects of SEQ ID NO 1 in Human PBMC from Steroid Resistant Asthmatics or Healthy Donors Cell Preparation Blood samples were obtained from healthy volunteers or steroid resistant asthmatics. PBMC were isolated by density gradient centrifugation using Ficoll-Paque Plus (Pharmacia Biotech, Uppsala, Sweden), washed three times in buffered saline solution (PBS), and re-suspended in RPMI 1640 (Sigma) containing 10% heat inactivated fetal calf serum (FCS) (Life Technologies), 100 U/mL penicillin 100 μg/mL streptomycin (Life Technologies), 2 mM L-glutamine (Sigma), gentamycin (Sigma) and 5 mM Hepes (Gibco, Life Technologies). Cells were counted using 0.4% Trypan blue solution (Sigma Aldrich)

In Vitro Stimulation

PBMC, prepared as previously described were, directly after seeding, stimulated with SEQ.ID.NO. 1. (25 μM and 100 μM) in the presence or absence of Dex ($10^{-6}$, $10^{-8}$ and $10^{-10}$ M) into a 96-well flat bottomed cell culture plate at 500 000 cells/well in RPMIc. As control ODN, 1 μM of IDX0910 was used. After treatment, cells were incubated in a humified incubator at 5% carbon dioxide and 37° C. for 48 hrs. Supernatants were saved and stored at −20° C. prior to cytokine level determination.

Cytometric Bead Array—CBA

The supernatants were kept at −20° C. until analyzed. IFN-, IL-6, IL-10, IL-2, IL-4 and TNF-alpha were measured utilizing the Cytometric Bead Array (CBA) from Becton Dickenson (BD), according to the manufacturer's protocol. The lower detection limit was 20 pg/ml for each cytokine. The FACSCalibur was used for all CBA analysis for this study.

Results Corresponding to Example 13

PBMCs were incubated in medium (basal) or with 25 μM (hatched bars) or 100 μM (dotted bars) of the CpG containing SEQ.ID.NO.1 for 48 hours before detection of IL-6 in supernatant. Each bar of the histogram represents average amount of IL-6 production from 9 healthy donors and 9 steroid resistant asthmatics. Experiments were performed in triplicate for each blood donor. Background levels of IL-6 (medium) were subtracted from each group of samples.

Figure 15:
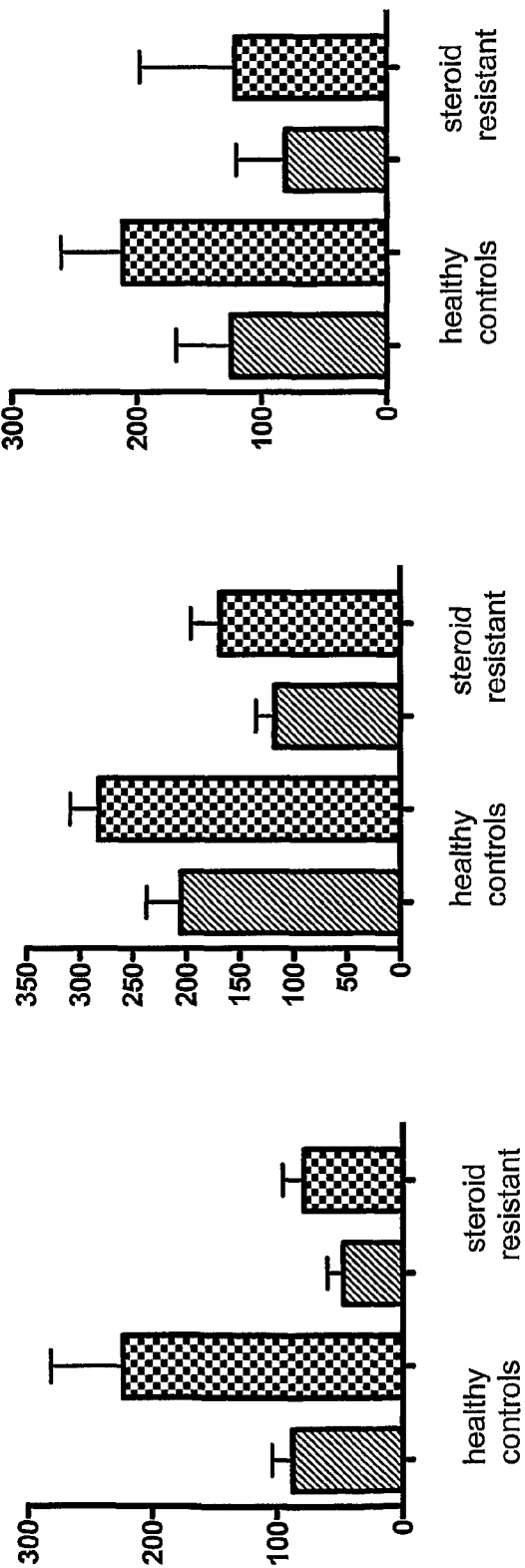
FIG. 15 shows the average amounts of a) IL-6, b) IL-10, and c) interferon-gamma production (pg/ml) in PBMC from healthy and steroid resistant asthmatics upon stimulation with SEQ.ID.NO.1

From FIG. 15, (a-c) there is a clear difference in response regarding the production of IL-6, IL-10 and interferon-gamma from PBMCs derived from healthy individuals and steroid resistant asthmatics. The levels of IL-6, IL-10 and interferon-gamma induced (pg/ml) is significantly lower in steroid resistant PBMCs when compared to those levels seen in healthy PBMCs. These results indicate a clear reduction in response of steroid resistant PBMCs to the effects of an immunomodulatory oligonucleotide as represented by SEQ.ID.NO.1.

Example 14

Human Pilot Proof of Concept Study in Steroid Resistant/Dependent Patients

A small pilot study was conducted in steroid refractory/dependent IBD patients with the following objectives.

Primary objective: To assess the safety issues regarding the use of the DNA based oligonucleotide denoted as SEQ.ID.NO.1 in ulcerative colitis and Crohn's disease patients.

Secondary objective: To explore the clinical efficacy as determined by endoscopic and clinical remission/improvement rates, histological improvement and changes in clinical laboratory parameters.

The study was placebo controlled; double blinded single dose and considered patients that were unresponsive to corticosteroids or corticosteroid dependent who where on concomitant steroid therapies.

Doses levels used were 3 mg and 30 mg given as a single rectal administration

Clinical response at week 1
i) SEQ.ID.NO.1 5/7 (71%) responders
ii) Placebo 1/4 (25%) responders Overall, this pilot study indicated good efficacy in both dose groups following a single rectal administration. More suspiring was the rapidity of response in that all responding patients did so within a week of receiving the study drug. Of interest was the finding that two from the 7 patients that received SEQ.ID.NO.1 are still as of today in remission and steroid free. Moreover, no serious adverse events were recorded.

Example 15

Clinical Phase II Study

A large 150 patient study performed in ulcerative colitis patients who were neither on concomitant steroid therapies nor were described as being steroid refractory/dependent.

Primary objective: To evaluate the ability of each of the four dose levels (0.3 mg, 3 mg, 30 mg and 100 mg) of oligonucleotide SEQ.ID.NO.1 as an anti-inflammatory therapy to induce clinical remission in patients with mild to moderately active ulcerative colitis (UC), as compared with placebo.

Secondary objective: To assess the tolerability of single rectal doses of SEQ.ID.NO.1 oligonucleotide and to further evaluate the efficacy and safety of SEQ.ID.NO.1 oligonucleotide at four dose levels and to assess the pharmacokinetics of SEQ.ID.NO.1 oligonucleotide after rectal administration, as compared to placebo.

Study Conclusions

| Clinical response at Week 1, ITT/Safety population | | | | | |
|---|---|---|---|---|---|
| Clinical Response | 0.3 mg (N = 31) | 3 mg (N = 29) | 30 mg (N = 30) | 100 mg (N = 29) | Placebo (N = 29) |
| Yes, n (%) | 8 (25.8) | 6 (20.7) | 7 (23.3) | 5 (17.2) | 11 (37.9) |
| No, n (%) | 23 (74.2) | 23 (79.3) | 23 (76.7) | 24 (82.8) | 18 (62.1) |

As seen from the table, the response rate to those receiving active drug was 22% (26/119), placebo was 38% (11/29).

This study could not confirm that one single dose of SEQ.ID.NO.1 oligonucleotide in doses from 0.3 to 100 mg in a 20 limited number of patients, can induce clinical, endoscopic or histopathological remissions or responses over a 12 week period, however, this study demonstrated a good safety profile of the drug.

In comparison, the clinical response rates at week 1 were found to be:

|  | Pilot study | Phase II |
|---|---|---|
| Active | 71% | 22% |
| Placebo | 25% | 38% |

Overall Conclusion

It is clear from in vitro studies that there is a difference in response in PBMCs derived from steroid resistant asthmatics when compared to healthy controls, following incubation with SEQ.ID.No.1. PBMCs derived from healthy subjects produce significantly more IL-16, IL-10 and interferon-gamma when incubated with SEQ.ID.NO.1 than was seen in steroid resistant PBMCs.

What is also apparent is that patients from the pilot study who were on concomitant medications and where resistant or dependent on corticosteroids had a much better response rate than those patients seen in phase II, In phase II the patients were neither on steroid medications during the duration of the study and were neither resistant nor dependent to steroid therapies.

The diverging clinical outcomes between the pilot study and the larger phase II study would suggest that patients that are resistant or dependent to corticosteroids and on concomitant corticosteroid therapy respond much more favourably to a single rectal dose of SEQ.ID.NO. 1 than those patients that are not. However, the immunomodulating action of CpG containing oligonucleotides as illustrated by SEQ.ID.NO.1 and outlined in the mentioned examples may have induce beneficial changes in the immune system resulting in a possible re-sensitization or potentiation to the anti-inflammatory effects of steroids. Furthermore, it has been demonstrated that SEQ.ID.NO.1 and other examples of immunomodulating oligonucleotides induce the simultaneous production of certain cytokines which have demonstrated efficacy in a number of human steroid resistant/dependent diseases. Hence by administering SEQ.ID.NO.1 to steroid resistant/dependent patients would have induced the endogenous production if interferons and IL-10 in those patients, and possible thereby increase the efficacy of the steroid treatment resulting in a dramatic improvement of the inflammatory condition.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

References

Adcock I M, Ito K and Barnes P J (2004). Glucocorticoids: effects on gene transcription. Proc. Am. Thoracic Soc. 1:247-54

Auphan N, DiDonato J A, Rosette C et al (1995). Immunosuppression by glucocorticoids: Inhibition of NF-κB activity through induction of IκB synthesis. Science. 270:286-90.

Bauer S, Wagner H (2002) Bacterial CpG-DNA licenses TLR9. Curr Top Microbiol Immunol. 270:145-54

Bauer M, Redecke V, Ellwart J W, Scherer B, Kremer J P, Wagner H, Lipford G B (2001). Bacterial CpG-DNA triggers activation and maturation of human CD11c-, CD123+dendritic cells. J Immunol. 166:5000-7.

Bennet J D and Brinkman M (1989). Treatment of ulcerative colitis by implantation of normal colonic flora. Lancet 1:164

Borody T J, Warren E F, Leis S, Surace R, Ashman O (2003). Treatment of ulcerative colitis using fecal bacteriotherapy. J Clin Gastroenterol. 37:42-7

Carstensen J T (1998). Pharmaceutical Preformulation. Taylor and Francis group. CRC press Chikanza I C, Kozaci D, Chernajovsky Y (2003). The molecular and cellular basis of corticosteroid resistance. J Endocrinol. 179:301-10

Eiseman B, Silen W, Bascom G S et al (1958). Fecal enema as an adjunct in the treatment of pseudomembranous enterocolitis. Surgery. 44:854-859

Gibson, M (2001). Pharmaceutical Preformulation and Formulation: A Practical Guide from Candidate Drug Selection to Commercial Dosage Form. Taylor and Francis group. CRC press Gill P S, Harrington W Jr, Kaplan M H, Ribeiro R C, Bennett J M, Liebman H A, Bernstein-Singer M, Espina B M, Cabral L, Allen S, et al (1995). Treatment of adult T-cell leukemia-lymphoma with a combination of interferon alfa and zidovudine. N Engl J Med. 332:1744-8

Hamid Q A, Wenzel S E, Hauk P J, Tsicopoulos A, Wallaert B, Lafitte J J, Chrousos G P, Szefler S J, Leung D Y (1999). Increased glucocorticoid receptor beta in airway cells of glucocorticoid-insensitive asthma. Am J Respir Crit Care Med. 159(5 Pt 1):1600-4

Hawrylowicz C M, O'Garra A (2005). Potential role of interleukin-10-secreting regulatory T cells in allergy and asthma. Nat Rev Immunol. 5:271-83

Hawrylowicz C M, Richards D, Loke T K, Corrigan C, Lee T (2002). A defect in corticosteroid-induced IL-10 production in T lymphocytes from corticosteroid-resistant asthmatic patients. J Allergy Clin Immunol. 109:369-70

Jahn-Schmid B, Wiedermann U, Bohle B, Repa A, Kraft D, Ebner C (1999). Oligodeoxynucleotides containing CpG motifs modulate the allergic TH2 response of BALB/c mice to Bet v 1, the major birch pollen allergen. J Allergy Clin Immunol. 104:1015-23

Klinman D M, Barnhart K M, Conover J (1999). CpG motifs as immune adjuvants. Vaccine. 17:19-25

Koh et al (2002). Current Biology 12,317-321

Krieg A M (2006). Therapeutic potential of Toll-like receptor 9 activation. Nat Rev Drug Discov. 5:471-84

Krieg A M, Yi A K, Matson S, Waldschmidt T J, Bishop G A, Teasdale R, Koretzky G A, Klinman D M (1995). CpG motifs in bacterial DNA trigger direct B-cell activation. Nature. 374:546-9

Lee V H, Yamaoto A and Kompella U B (1991). Mucosal penetration enhancers for facilitation of peptide and protein drug absorption. Crit Rev Ther Drug Carrier Syst. 8:91-192

Leung D Y, Szefler S J. New insights into steroid resistant asthma. Pediatr Allergy Immunol. 1998 February;9(1):3-12

Musch E, Andus T, Malek M (2002). Induction and maintenance of clinical remission by interferon-beta in patients with steroid-refractory active ulcerative colitis-an open long-term pilot trial. Aliment Pharmacol Ther. 16:1233-9

Naseer T, Minshall E M, Leung D Y, Laberge S, Ernst P, Martin R J, Hamid Q (1997). Expression of IL-12 and IL-13 mRNA in asthma and their modulation in response to steroid therapy. Am J Respir Crit Care Med. 155:845-51

Niederau C, Heintges T, Lange S, Goldmann G, Niederau C M, Mohr L, Haussinger D (1996). Long-term follow-up of HBeAg-positive patients treated with interferon alfa for chronic hepatitis B. N EngI J Med. 1996 334:1422-7

Richards D F, Fernandez M, Caulfield J, Hawrylowicz C M (2005). Glucocorticoids drive human CD8(+) T cell differentiation towards a phenotype with high IL-10 and reduced IL-4, IL-5 and IL-13 production. Eur J Immunol. 30:2344-54

Scheinman R I, Cogswell P C, Lofquist A K et al (1995). Role of transcriptional activation of IκBα in mediation of immunosuppression by glucocorticoids. Science. 270:283-6

Simon H U, Seelbach H, Ehmann R, Schmitz M (2003). Clinical and immunological effects of low-dose IFN-alpha treatment in patients with corticosteroid-resistant asthma. Allergy. 58:1250-5

Sousa A R, Lane S J, Cidlowski J A, Staynov D Z, Lee T H (2000). Glucocorticoid resistance in asthma is associated with elevated in vivo expression of the glucocorticoid receptor beta-isoform. J Allergy Clin Immunol. 105:943-50

Stelmach I, Jerzynska J, Kuna P (2002). A randomized, double-blind trial of the effect of glucocorticoid, antileukotriene and beta-agonist treatment on IL-10 serum levels in children with asthma. Clin Exp Allergy. 32:264-9

Sumer N, Palabiyikoglu M (1995). Induction of remission by interferon-alpha in patients with chronic active ulcerative colitis. Eur J Gastroenterol Hepatol. 7:597-602

Taniguchi T and Takaoka A (2001). A weak signal for strong responses: interferon-alpha/beta revisited. Nat Rev Mol Cell Biol. 2:378-86

Tighe H, Takabayashi K, Schwartz D, Marsden R, Beck L, Corbeil J, Richman D D, Eiden J J Jr, Spiegelberg H L, Raz E (2000). Conjugation of protein to immunostimulatory DNA results in a rapid, long-lasting and potent induction of cell-mediated and humoral immunity. Eur J Immunol. 30:1939-47

Tokunaga T, Yano O, Kuramoto E, Kimura Y, Yamamoto T, Kataoka T, Yamamoto S (1992). Synthetic oligonucleotides with particular base sequences from the cDNA encoding proteins of Mycobacterium bovis BCG induce interferons and activate natural killer cells. Microbiol Immunol. 36:55-66

Tomita K, Lim S, Hanazawa T, Usmani O, Stirling R, Chung K F, Barnes P J, Adcock I M (2002). Attenuated production of intracellular IL-10 and IL-12 in monocytes from patients with severe asthma. Clin Immunol. 102:258-66

Tormey V J, Leonard C, Faul J, Bernard S, Burke C M, Poulter L W (1998). Deregulations of monocyte differentiation in asthmatic subjects is reversed by IL-10. Clin Exp Allergy. 28:992-8

Xystrakis E, Kusumakar S, Boswell S, Peek E, Urry Z, Richards D F, Adikibi T, Pridgeon C, Dallman M, Loke T K, Robinson D S, Barrat F J, O'Garra A, Lavender P, Lee T H, Corrigan C, Hawrylowicz C M (2006). Reversing the defective induction of IL-10-secreting regulatory T cells in glucocorticoid-resistant asthma patients. J Clin Invest. 116:146-55

Yamamoto S, Yamamoto T, Kataoka T, Kuramoto E, Yano O, Tokunaga T (1992). Unique palindromic sequences in synthetic oligonucleotides are required to induce IFN [correction of INF] and augment IFN-mediated [correction of INF] natural killer activity. J Immunol. 148:4072-6

Zeuzem S, Feinman S V, Rasenack J, Heathcote E J, Lai M Y, Gane E, O'Grady J, Reichen J, Diago M, Lin A, Hoffman J, Brunda M J (2000). Peginterferon alfa-2a in patients with chronic hepatitis C. N Engl J Med. 343:1666-7

The invention claimed is:

1. A method for enhancing steroid efficacy in a steroid refractory patient afflicted with an airway inflammatory condition and currently on steroid anti-inflammatory treatment but not responding or responding poorly or inadequately to the steroid anti-inflammatory treatment, or a steroid dependent patient afflicted with an airway inflammatory condition and currently on and responding adequately to steroid anti-inflammatory treatment, with the inability to be weaned off systemically or topically administered steroid treatment without increasing severity of the airway inflammatory condition, comprising:

administering to the patient afflicted with an airway inflammatory condition an oligonucleotide which alone does not provide effective treatment for the airway inflammatory condition in a patient that is not steroid refractory, the oligonucleotide having the sequence 5'-X$_m$CG-Y$_n$-3', wherein X is A, T, C or G, Y is A, T, C or G, m=1-30, n=1-30, and the total length of the oligonucleotide is 8-40 nucleotides, wherein at least one CG dinucleotide is unmethylated, and wherein the oligonucleotide is administered in an amount effective to improve sensitivity of the patient to the steroid anti-inflammatory treatment and thereby induce a clinical response to the steroid anti-inflammatory treatment.

2. The method according to claim 1, wherein m is 1-20 and n is 1-20.

3. The method according to claim 1, wherein m is 1-12 and n is 1-12.

4. The method according to claim 1, wherein m is 1-10 and n is 1-10.

5. The method according to claim 1, wherein m is 1-8 and n is 1-8.

6. The method according to claim 1, wherein m is 1-6 and n is 1-6.

7. The method according to claim 1, wherein m is 1-4 and n is 1-4.

8. The method according to claim 1, wherein m is 1-2 and n is 1-2.

9. The method according to claim 1, wherein the inflammatory condition is selected from the group consisting of Addison's disease, adult respiratory distress syndrome, chronic obstructive pulmonary disease (COPD), allergy and asthma.

10. The method according to claim 1, wherein the inflammatory condition is asthma.

11. The method according to claim 1, wherein at least one nucleotide has a phosphate backbone modification.

12. The method according to claim 11, wherein the phosphate backbone modification is a phosphorothioate or phosphorodithioate modification.

13. The method according to claim 11, wherein the phosphate backbone modification is on 5' and/or 3' inter-nucleotide linkages.

14. The method according to claim 11, wherein the modification occurs at one or more nucleotides at any position along the entire length of said oligonucleotide.

15. The method according to claim 1, wherein said oligonucleotide is an oligonucleotide composed of DNA or an analogue or mimic of DNA.

16. The method according to claim 15, wherein said oligonucleotide is an oligonucleotide composed of DNA or an analogue or mimic of DNA selected from the group consisting of methylphosphonate, N3→P5'-phosphoramidate, morpholino, peptide nucleic acid (PNA), locked nucleic acid (LNA), arabinosyl nucleic acid (ANA), fluoro-arabinosyl nucleic acid (FANA), and methoxy-ethyl nucleic acid (MOE).

17. The method according to claim 1, wherein said oligonucleotide comprises at least one modified sugar moiety nucleobase.

18. The method according to claim 17, wherein the modified sugar moiety is a 2'-O-methoxyethyl sugar moiety.

19. The method according to claim 1, wherein said oligonucleotide is a branched oligonucleotide, comprising at least one additional nucleic acid moiety, wherein at least one nucleic acid moiety comprises the sequence 5'-CG-3'.

20. The method according to claim 1, wherein the oligonucleotide is administered in combination with a steroid.

21. The method according to claim 1, wherein the amount of oligonucleotide administered to the patient is about 0.01 μg to about 100 mg per kg body weight.

22. The method according to claim 1, wherein the amount of oligonucleotide administered to the patient is about 0.1 μg to about 10 mg per kg body weight.

23. The method according to claim 1, wherein the amount of oligonucleotide administered to the patient is about 1 μg to about 5 mg per kg body weight.

24. The method according to claim 1, wherein the oligonucleotide is administered via inhalation, or opthalmically, intranasally, parenterally, orally, intradermally, or rectally.

25. The method according to claim 1, wherein the patient is human.

26. The method according to claim 1 wherein the oligonucleotide is not more than 30 nucleotides in length.

27. The method according to claim 1 wherein the oligonucleotide is not more than 24 nucleotides in length.

28. The method according to claim 1, wherein the steroid and the oligonucleotide are administered simultaneously, substantially simultaneously or sequentially.

29. The method according to claim 1, wherein the steroid and oligonucleotide are administered temporally spaced and up to several months apart.

30. The method according to claim 1, wherein said patient is currently on nonsteroidal anti-inflammatory treatment.

31. The method according to claim 1, wherein the oligonucleotide is administered as a single administration.

32. The method according to claim 1, wherein the oligonucleotide is administered in more than a single administration.

33. The method according to claim 1, wherein the oligonucleotide consists of the sequence:
5'-GGAACAGTTCGTCCATGGC-3' (SEQ ID NO: 1).

34. The method according to claim 33, wherein the inflammatory condition is selected from the group consisting of Addison's disease, adult respiratory distress syndrome, chronic obstructive pulmonary disease (COPD), allergy and asthma.

35. The method according to claim 33, wherein the inflammatory condition is asthma.

36. The method according to claim 33, wherein the steroid and the oligonucleotide are administered simultaneously, substantially simultaneously or sequentially.

37. The method according to claim 33, wherein the steroid and oligonucleotide are administered temporally spaced and up to several months apart.

38. The method according to claim 33, wherein said patient is currently on nonsteroidal anti-inflammatory treatment.

39. The method according to claim 33, wherein at least one nucleotide has a phosphate backbone modification.

40. The method according to claim 39, wherein the phosphate backbone modification is a phosphorothioate or phosphorodithioate modification.

41. The method according to claim 39, wherein the phosphate backbone modification is on 5' and/or 3' inter-nucleotide linkages.

42. The method according to claim 39, wherein the modification occurs at one or more nucleotides at any position along the entire length of said oligonucleotide.

43. The method according to claim 33, wherein said oligonucleotide is an oligonucleotide composed of DNA or an analogue or mimic of DNA.

44. The method according to claim 43, wherein said oligonucleotide is an oligonucleotide composed of DNA or an analogue or mimic of DNA selected from the group consisting of methylphosphonate, N3→P5'-phosphoramidate, morpholino, peptide nucleic acid (PNA), locked nucleic acid (LNA), arabinosyl nucleic acid (ANA), fluoro-arabinosyl nucleic acid (FANA), and methoxy-ethyl nucleic acid (MOE).

45. The method according to claim 33, wherein said oligonucleotide comprises at least one modified sugar moiety nucleobase.

46. The method according to claim 45, wherein the modified sugar moiety is a 2'-O-methoxyethyl sugar moiety.

47. The method according to claim 1, wherein said oligonucleotide is a branched oligonucleotide, comprising at least one additional nucleic acid moiety, wherein at least one nucleic acid moiety comprises the sequence 5'-CG-3'.

48. The method according to claim 33, wherein the oligonucleotide is administered in combination with a steroid.

49. The method according to claim 33, wherein the amount of oligonucleotide administered to the patient is about 0.01 μg to about 100 mg per kg body weight.

50. The method according to claim 33, wherein the amount of oligonucleotide administered to the patient is about 0.1 μg to about 10 mg per kg body weight.

51. The method according to claim 33, wherein the amount of oligonucleotide administered to the patient is about 1 µg to about 5 mg per kg body weight.

52. The method according to claim 33, wherein the oligonucleotide is administered via inhalation, or opthalmically, intranasally, parenterally, orally, intradermally, or rectally.

53. The method according to claim 33, wherein the oligonucleotide is administered as a single administration.

54. The method according to claim 33, wherein the oligonucleotide is administered in more than a single administration.

55. The method according to claim 33, wherein the patient is a steroid refractory patient afflicted with an airway inflammatory condition and currently on steroid anti-inflammatory treatment but not responding or responding poorly or inadequately to the steroid anti-inflammatory treatment.

56. The method according to claim 33, wherein the patient is a steroid dependent patient afflicted with an airway inflammatory condition and currently on and responding adequately to steroid anti-inflammatory treatment, with the inability to be weaned off systemically or topically administered steroid treatment without increasing severity of the airway inflammatory condition.

57. The method according to claim 1, wherein the patient is a steroid refractory patient afflicted with an airway inflammatory condition and currently on steroid anti-inflammatory treatment but not responding or responding poorly or inadequately to the steroid anti-inflammatory treatment.

58. The method according to claim 1, wherein the patient is a steroid dependent patient afflicted with an airway inflammatory condition and currently on and responding adequately to steroid anti-inflammatory treatment, with the inability to be weaned off systemically or topically administered steroid treatment without increasing severity of the airway inflammatory condition.

* * * * *

SEQUENCE LISTING

```
<160> NUMBER OF SEQ ID NOS: 8

<210> SEQ ID NO 1
<211> LENGTH: 19
<212> TYPE: DNA
<213> ORGANISM: Artificial sequence
<220> FEATURE:
<223> OTHER INFORMATION: Synthetic construct

<400> SEQUENCE: 1
ggaacagttc gtccatggc                                                19

<210> SEQ ID NO 2
<211> LENGTH: 19
<212> TYPE: DNA
<213> ORGANISM: Artificial sequence
<220> FEATURE:
<223> OTHER INFORMATION: Synthetic construct

<400> SEQUENCE: 2
ggaacagttg ctccatggc                                                19

<210> SEQ ID NO 3
<211> LENGTH: 19
<212> TYPE: DNA
<213> ORGANISM: Artificial sequence
<220> FEATURE:
<223> OTHER INFORMATION: Synthetic construct

<400> SEQUENCE: 3
gaaacagatc gtccatggt                                                19
```

```
<210> SEQ ID NO 4
<211> LENGTH: 19
<212> TYPE: DNA
<213> ORGANISM: Artificial sequence
<220> FEATURE:
<223> OTHER INFORMATION: Synthetic construct

<400> SEQUENCE: 4
gaaacagatg ctccatggt                                                  19

<210> SEQ ID NO 5
<211> LENGTH: 19
<212> TYPE: DNA
<213> ORGANISM: Artificial sequence
<220> FEATURE:
<223> OTHER INFORMATION: Synthetic construct

<400> SEQUENCE: 5
agctgagtag cctatagac                                                  19

<210> SEQ ID NO 6
<211> LENGTH: 20
<212> TYPE: DNA
<213> ORGANISM: Artificial sequence
<220> FEATURE:
<223> OTHER INFORMATION: Synthetic construct

<400> SEQUENCE: 6
ggtgcatcga tgcagggggg                                                 20

<210> SEQ ID NO 7
<211> LENGTH: 20
<212> TYPE: DNA
<213> ORGANISM: Artificial sequence
<220> FEATURE:
<223> OTHER INFORMATION: Synthetic construct

<400> SEQUENCE: 7
tccatgacgt tcctgacgtt                                                 20

<210> SEQ ID NO 8
<211> LENGTH: 24
<212> TYPE: DNA
<213> ORGANISM: Artificial sequence
<220> FEATURE:
<223> OTHER INFORMATION: Synthetic construct

<400> SEQUENCE: 8
tcgtcgtttt gtcgttttgt cgtt                                            24
```